US011854217B2

(12) United States Patent
Rodriguez et al.

(10) Patent No.: US 11,854,217 B2
(45) Date of Patent: Dec. 26, 2023

(54) CO-REGISTRATION OF CARDIAC IMAGES

(71) Applicant: KONINKLIJKE PHILIPS N.V., Eindhoven (NL)

(72) Inventors: Haim Rodriguez, Caesaria (IL); Eli Dichterman, Caesaria (IL); Yitzhack Schwartz, Caesaria (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 225 days.

(21) Appl. No.: 17/052,492

(22) PCT Filed: May 3, 2019

(86) PCT No.: PCT/EP2019/061409
§ 371 (c)(1),
(2) Date: Nov. 2, 2020

(87) PCT Pub. No.: WO2020/224744
PCT Pub. Date: Nov. 12, 2020

(65) Prior Publication Data

US 2022/0051421 A1 Feb. 17, 2022

(51) Int. Cl.
*G06T 7/33* (2017.01)
*A61B 18/14* (2006.01)
*A61B 18/00* (2006.01)

(52) U.S. Cl.
CPC ............ *G06T 7/33* (2017.01); *A61B 18/1492* (2013.01); *A61B 2018/00351* (2013.01);
(Continued)

(58) Field of Classification Search
CPC ............. G06T 7/33; G06T 2207/20101; G06T 2207/30048; G06T 3/0068;
(Continued)

(56) References Cited

U.S. PATENT DOCUMENTS 11,544,847 B1 * 1/2023 Jain .................. A61M 25/0127
11,622,669 B2 * 4/2023 Duindam ............... G06T 7/337 600/424
(Continued)

FOREIGN PATENT DOCUMENTS

WO 2018120974 A1 7/2018

OTHER PUBLICATIONS

Brooks, Dana et al., Electrical Imaging of the Heart, 1997, IEEE, IEEE Signal Processing Magazine, pp. 24-42 (Year: 1997).*
(Continued)

*Primary Examiner* — Lewis G West

(57) ABSTRACT

Systems, devices, and methods for co-registering electro-anatomical images are provided. In one embodiment of the present disclosure, treatment locations are displayed to the physician on an image of the remodeled heart by co-registering first and second electro-anatomical images based on: (1) a first electro-anatomical image of an anatomy, (2) treatment location data indicating treatment locations with respect to the first electro-anatomical image, (3) a second electro-anatomical image of the anatomy after the anatomy has remodeled, and (4) a non-rigid transformation that transforms the first electro-anatomical image to the second electro-anatomical image of the remodeled anatomy. The non-rigid transformation is applied to the treatment location data to map the treatment locations to the second electro-anatomical image of the remodeled anatomy.

19 Claims, 16 Drawing Sheets

400

410 Receive a first electro-anatomical image of an anatomy

420 Receive treatment location data associated with the first electro-anatomical image and indicative of treatment locations on the anatomy 430 Receive a second electro-anatomical image of the anatomy after treatment 440 Determine a non-rigid transformation that transforms the first electro-anatomical image to the second electro-anatomical image 450 Apply the non-rigid transformation to the treatment location data to map the treatment locations to the second electro-anatomical image of the anatomy 460 Display the treatment locations mapped to the second electro-anatomical image of the anatomy

(52) U.S. Cl.
CPC ............... *A61B 2018/00577* (2013.01); *A61B 2018/00839* (2013.01); *G06T 2207/20101* (2013.01); *G06T 2207/30048* (2013.01)

(58) Field of Classification Search
CPC ...... A61B 18/1492; A61B 2018/00351; A61B 2018/00577; A61B 2018/00839; A61B 5/287; A61B 2018/00357; A61B 2090/364
See application file for complete search history.

(56) References Cited

U.S. PATENT DOCUMENTS

2006/0002615 A1* 1/2006 Fu .............................. G06T 7/33 382/254
2006/0002631 A1* 1/2006 Fu .............................. G06T 7/32 382/128
2007/0299351 A1* 12/2007 Harlev .................. A61B 5/339 600/509
2008/0218509 A1* 9/2008 Voth ....................... G06T 17/20 345/419
2008/0273779 A1 11/2008 Pekar
2015/0010223 A1 1/2015 Sapiro
2015/0366523 A1* 12/2015 Ben-Haim ......... G01N 33/6896 600/431
2017/0325891 A1* 11/2017 Harlev .................... G06T 17/20
2018/0125575 A1 5/2018 Schwartz
2018/0194024 A1 7/2018 Teteak
2018/0199990 A1 7/2018 Monir
2018/0211389 A1 7/2018 Auvray
2019/0340838 A1 11/2019 Gluhovsky
2020/0000526 A1* 1/2020 Zhao ...................... A61B 34/35
2020/0046431 A1* 2/2020 Soper ..................... A61B 34/20
2020/0085504 A1* 3/2020 Schwartz ............... A61B 34/20
2020/0197106 A1* 6/2020 Dekel .................... A61B 34/20
2021/0154496 A1* 5/2021 Maurer ................ A61N 5/1037
2021/0174940 A1* 6/2021 Rodriguez ............. G06T 17/20
2023/0061771 A1* 3/2023 Zhao ...................... A61B 34/37

OTHER PUBLICATIONS

International Search Report & Written Opinion for PCT/EP2019/061409, dated Nov. 29, 2019.

Del Greco, Maurizio et al "Image Fsion Shows the Role of Incomplete Ablation Lines in Creating a Sbstrate for left Atrial Fltter Occurring After Atrial Fibrillation Ablation", Heart Rhythm, vol. 5, No. 1, Jan. 2008.

Rettmann, M.E. et al "Deformable Registration of Radiation Isodose Lines to Delayed Contrast-Enhanced Magnetic Resonance Images for Assessment of Myocardial Lesion Formation Following Proton Beam Therapy", Progress in Biomedical Optics and Imaging, vol. 10576, Mar. 2018.

* cited by examiner

CO-REGISTRATION OF CARDIAC IMAGES

FIELD OF THE INVENTION

The present disclosure relates generally to electromagnetic imaging and, in particular, to co-registering images of an anatomy that includes determining a transformation from a first image of the anatomy to a second image of the anatomy. For example, an electro-anatomical imaging system can receive electro-anatomical images from a sensing catheter carrying a plurality of electrodes to generate electro-anatomical images, and co-register the electro-anatomical images by applying a non-rigid transformation.

BACKGROUND OF THE INVENTION

Atrial fibrillation (AF) is an abnormal heart rhythm characterized by rapid and irregular beating of the atria, and may be associated with heart palpitations, fainting, lightheadedness, shortness of breath, or chest pain. The disease is associated with an increased risk of heart failure, dementia, and stroke. AF is sometimes caused by electrical pulses generated by secondary pacers at the ostium of the pulmonary veins. Accordingly, one way of treating AF is by pulmonary vein isolation, which can include ablating the inner wall of the left atrium to form lesions that isolate the ostium of the pulmonary veins from the rest of the left atrium.

After ablation, edema developed during ablation is absorbed in the walls of the LA, scars develop at the lesioned cites, and in many cases the structure of the left atrium remodels. In some cases, about a month after the ablation treatment, atrial fibrillation returns, because the isolation of the pulmonary veins is less tight in the remodeled heart than it was during ablation (i.e., in the original heart, before remodeling). When atrial fibrillation returns after ablation, it may be possible to treat it by a second ablation procedure (also known as re-do) to close gaps in the isolating tissue generated by the original ablation procedure. In such procedures, the physician searches for gaps in the electrically isolating tissue, and ablates at such gaps to close them. The search for gaps is done by pacing, which involves transmitting an electrical signal from an ostium of a pulmonary vein and checking if and where the signal arrives across the alleged isolation.

SUMMARY OF THE INVENTION

An aspect of some embodiments of the present disclosure includes guiding a physician in finding gaps in isolating tissue, so as to facilitate closing of these gaps by ablation. In one embodiment of the present disclosure, the physician is presented with an image of the patient's remodeled heart, on which the location of the lesions ablated during the first intervention are marked. Although it may be impossible to visually distinguish between normal and isolating tissue in electro-anatomical images, the locations ablated in the first intervention can be shown on an image of the remodeled heart, based on lesion locations in the original heart and a registration transform, transforming locations in the original heart to locations in the restructured heart, so that the physician can see the ablations positioned on the restructured heart. This way, the physician may find the gaps and re-do the ablation more efficiently than by pacing, or at least can pace only in some locations suspected for poor isolation rather than blindly pacing the entire circumference of the PV ostium.

In some embodiments, during the first intervention, the locations of the lesions are recorded in reference to the image from the first procedure, and this image is registered to an image of the remodeled heart, so that the recorded lesions can be marked on the remodeled heart. The registering is used to tell the location of the lesions in the remodeled heart based on the records taken during the first procedure. Thus, in some embodiments, the lesions are displayed to the physician on an image of the remodeled heart based on: (1) a first image, which is an image of the original heart; (2) records of lesioned locations in the original heart; (3) a second image, which is an image of the remodeled heart; and (4) a registration transform, transforming points in the recorded locations of the lesions to corresponding points in the remodeled heart.

According to one embodiment of the present disclosure, a system for co-registering electro-anatomical images includes a user display and a processor circuit in communication with the user display. The processing circuit is configured to: receive a first electro-anatomical image of an anatomy, the first electro-anatomical image generated based on electro-anatomical data obtained using two or more electrodes positioned on a catheter; receive treatment location data indicating treatment locations with respect to the first electro-anatomical image, the treatment location data based on the electro-anatomical data obtained using the two or more electrodes positioned on the catheter; receive a second electro-anatomical image of the anatomy after the anatomy has remodeled; determine a non-rigid transformation that transforms the first electro-anatomical image to the second electro-anatomical image of the remodeled anatomy; apply the non-rigid transformation to the treatment location data to map the treatment locations to the second electro-anatomical image of the remodeled anatomy; and display the treatment locations mapped to the second electro-anatomical image on the user display.

In some embodiments, the processor circuit is configured to determine the non-rigid transformation based on known distance(s) between the two or more electrodes on the catheter. In some embodiments, the processor circuit is configured to determine the non-rigid transformation based on a probabilistic correspondence model that assigns a probability of correspondence between a first point in the first electro-anatomical image and a second point in the second electro-anatomical image, and wherein the probabilistic correspondence model comprises a coherence condition in which a greater probability of correspondence is assigned to points near a same anatomical landmark identified in each of the first and second electro-anatomical images. In still other embodiments, the processor circuit is configured to: identify a landmark in the first electro-anatomical image; identify the landmark in the second electro-anatomical image; and determine the non-rigid transformation based on the landmark identified in the first and second electro-anatomical images. In some aspects, the system further includes a user input device in communication with the processor circuit, wherein the processor circuit is configured to: receive, from the user input device, a first input indicating a location of the landmark in the first electro-anatomical image; receive, from the user input device, a second input indicating a location of the landmark in the second electro-anatomical image; and determine the non-rigid transformation based on the received first and second inputs.

In other aspects, the processor circuit is configured to: associate, with respect to the first electro-anatomical image, a first plurality of electro-anatomical data points with a first catheter track; associate, with respect to the second electro-anatomical image, a second plurality of electro-anatomical data points with a second catheter track, wherein the first catheter track is aligned with the second catheter track; and determine the non-rigid transformation based on a correspondence between the first and second catheter tracks. In some embodiments, the system further includes a user input device in communication with the processor circuit, wherein the processor circuit is configured to: receive, from the user input device, a first plurality of inputs indicating locations of the catheter while traveling along the first catheter track; receive, from the user input device, a second plurality of inputs indicating locations of the catheter while traveling along the second catheter track; and determine the non-rigid transformation based on the first and second pluralities of inputs.

In some embodiments, the first electro-anatomical image comprises a first three-dimensional point cloud image of the anatomy, the second electro-anatomical image comprises a second three-dimensional point cloud image of the anatomy, and the processor circuit is configured to: determine the transformation by registering points of the first point cloud image to corresponding points of the second point cloud image; and generate a reconstructed three-dimensional image based on the registered points of the first and second cloud images. In some aspects, the processor circuit is configured to determine the transformation based on natural inter-point distances. In some aspects, the processor circuit is configured to segment each of the first and second electro-anatomical images into a plurality of segments. In a further aspect, the processor circuit is configured to: assign the points of the first point cloud image to a segment; assign the corresponding points of the second point cloud image to the same segment; and determine the transformation such that the points in the first point cloud image are transformed to the same segment in the second point cloud image. In some embodiments, the processor circuit is configured to: detect a physiological rhythm change in the anatomy, wherein the second electro-anatomical image represents the anatomy exhibiting the changed physiological rhythm.

According to another embodiment of the present disclosure, a method for co-registering electro-anatomical images includes: receiving, at a processor circuit in communication with a user display, a first electro-anatomical image of an anatomy, the first electro-anatomical image generated based on electro-anatomical data obtained using two or more electrodes positioned on a catheter; receiving, at the processor circuit, treatment location data indicating treatment locations with respect to the first electro-anatomical image, the treatment location data based on the electro-anatomical data obtained using the two or more electrodes positioned on the catheter; receiving, at the processor circuit, a second electro-anatomical image of the anatomy after the anatomy has remodeled; determining a non-rigid transformation that transforms the first electro-anatomical image to the second electro-anatomical image of the remodeled anatomy; applying the non-rigid transformation to the treatment location data to map the treatment locations to the second electro-anatomical image of the remodeled anatomy; and displaying the treatment locations mapped to the second electro-anatomical image on the user display.

In some embodiments, determining the non-rigid transformation comprises determining the non-rigid transformation based on known distance(s) between the two or more electrodes on the catheter. In some embodiments, determining the non-rigid transformation comprises determining the non-rigid transformation based on a probabilistic correspondence model that assigns a probability of correspondence between a first point in the first electro-anatomical image and a second point in the second electro-anatomical image, and wherein the probabilistic correspondence model comprises a coherence condition in which a greater probability of correspondence is assigned to points near a same anatomical landmark identified in each of the first and second electro-anatomical images. In some embodiments, the method further includes identifying a landmark in the first electro-anatomical image; identifying the landmark in the second electro-anatomical image; and determining the non-rigid transformation based on the landmark identified in the first and second electro-anatomical images.

In some aspects, the method further includes: associating, with respect to the first electro-anatomical image, a first plurality of electro-anatomical data points with a first catheter track; associating, with respect to the second electro-anatomical image, a second plurality of electro-anatomical data points with a second catheter track, wherein the first catheter track is aligned with the second catheter track; and determining the non-rigid transformation based on a correspondence between the first and second catheter tracks. In some embodiments, receiving the first electro-anatomical image comprises receiving a first three-dimensional point cloud image of the anatomy, wherein receiving the second electro-anatomical image comprises receiving a second three-dimensional point cloud image of the anatomy, and wherein the method further comprises: determining the transformation by registering points of the first point cloud image to corresponding points of the second point cloud image; and generating a reconstructed three-dimensional image based on the registered points of the first and second cloud images. In some embodiments, the method further includes detecting a physiological rhythm change in the anatomy, wherein the second electro-anatomical image represents the anatomy exhibiting the changed physiological rhythm Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION OF THE EMBODIMENTS

Figure 1B:
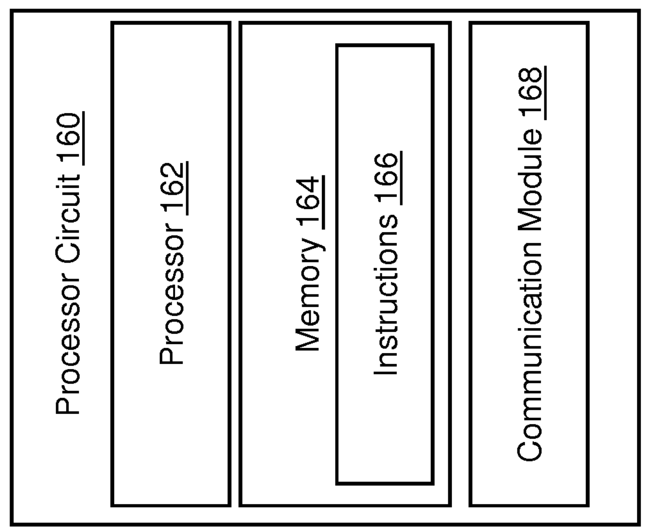
FIG. 1B is a schematic diagram of a processor circuit, according to embodiments of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

Figure 1A:
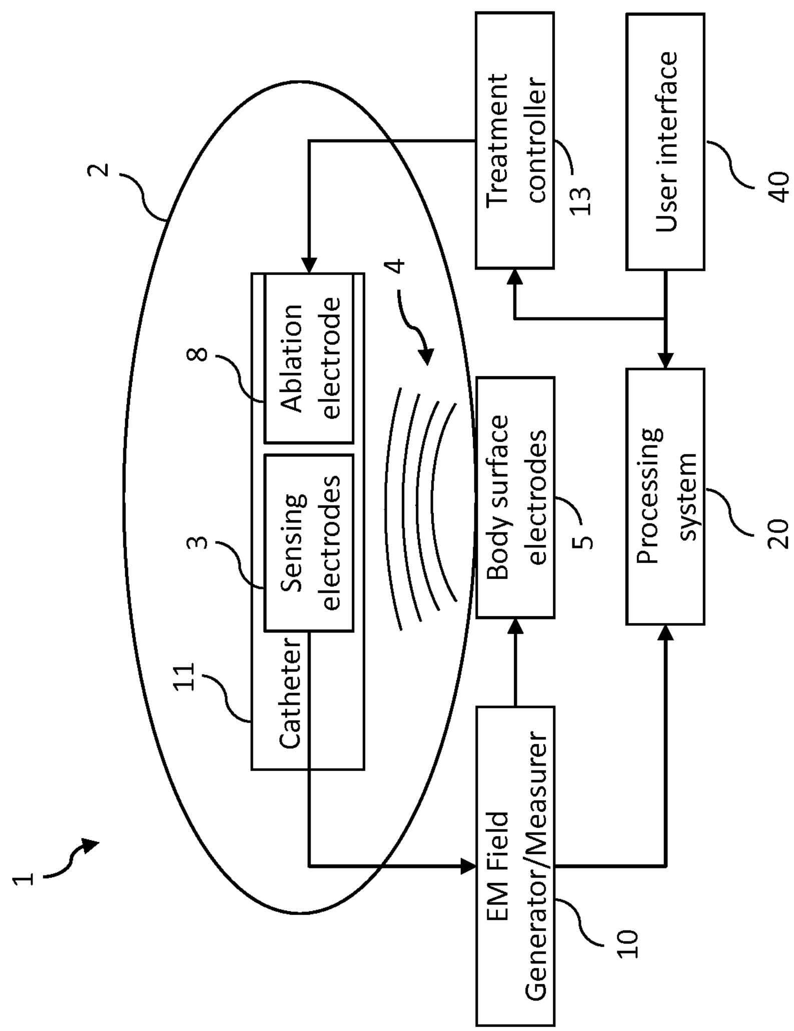
FIG. 1A is a diagrammatic schematic view of an electro-anatomical imaging system, according to aspects of the present disclosure.

Reference is now made to FIG. 1A, which schematically represents a navigation and treatment system 1 used with a processing system 20 or controller, according to some exemplary embodiments of the present disclosure. It will be understood that the processing system 20 may comprise a single processing or hardware component, or various hardware components configured to execute instructions saved to a memory. For example, processing system 20 may be configured to receive inputs from user interface 40 and measurements or data from EM field generator/measurer 10, and control the EM field generator/measurer 10 and treatment controller 13. The system 1 is configured to obtain electro-anatomical data to generate three-dimensional electro-anatomical images of the anatomy (e.g., an interior of a heart).

In some embodiments, the system 1 is configured to induce or generate at least one time-varying electromagnetic (EM) field 4 (for example, three or more crossing electromagnetic fields, each of a different frequency) using an electromagnetic field generator/measurer 10 (which is optionally itself comprised of a plurality of field generation modules) using electrodes such as body surface electrodes 5 across a region of anatomy 2 that is targeted to be navigated by catheter 9 comprising catheter probe 11. The catheter probe 11 may be in communication with the processing system 20 or processing circuit, and can include a flexible elongate member sized, shaped, structurally arranged, and/or otherwise configured to be positioned within a body lumen of a patient, such as a blood vessel. In particular, the distal portion of the catheter can include electrodes, sensors, or other electronic components configured to be positioned within the body lumen to sense, image, and/or perform therapeutic procedures within the body lumen. A proximal portion of the catheter can be positioned outside the body of the patient, and can be coupled to an interface for electrical communication within the processing system 20 and/or EM field generator/measurer. The catheter can include one or more communication lines, such as electrical conductors and/or fiber optic cables, positioned within the flexible elongate member and configured to communicatively couple the electrodes, sensors, and/or other electronic components to the interface.

The system can also include a treatment electrode 8 or ablation electrode controllable by the processing system 20 to perform ablation on a region of tissue in the anatomy 2. It will be understood that, in some embodiments, the ablation electrode 8 and the electrode 3 can be the same electrode. Herein, examples shown with respect to a catheter probe 11 should be understood to be optionally applicable to any navigable intrabody probe 11 suitably configured for obtaining electromagnetic field voltage readings by at least two sensors distanced from each other by a known distance. Typically, the time varying electromagnetic field is induced with a total inter-electrode voltage (body surface-to-body surface) of one volt or less, at a frequency of between about 10 kHz and about 1 MHz. A user interface 40 can be used, in some embodiments, in the initiating and stopping of workflows, identification of landmarks, identification of catheter tracks, treatment locations, and other functions.

In some embodiments, position data is acquired from an intrabody probe (e.g., catheter probe 11), from each of a plurality (e.g., 2, 3, 4 or more) of sensing electrodes 3 on the probe which act as sensors to measure electromagnetic field data indicative of position. The electrodes 3 can be controlled by and/or in communication with the processing system 20 to obtain the electromagnetic field data, such as electro-anatomical data. In some embodiments of the disclosure, the sensing electrodes 3 are in a known spacing relative to one another; for example, fixed at certain distances from one another. Alternatively, if the sensing electrode 3 spacing is dynamic (e.g. because the probe 11 can bend), the spacing can be estimated to change in correlation with parameters of probe operation (e.g., active deformation) and/or measured contact (e.g., deformation correlated with measurements of contact force). The known spacing is used, in some embodiments, as part of the data used in the reconstruction of the body cavity (e.g., a lumen of a hollow organ such as a heart chamber) within which the intrabody probe moves. For example, the catheter probe 11 can be used within a blood vessel, heart chambers, and/or any other suitable body cavity or area of the anatomy to generate electro-anatomical images. In some embodiments, position data is received by computer circuitry, e.g., from the sensors in real time or from a computer memory that saves data received from the sensors.

In some embodiments, a probe 11 having 2, 3, 4, 5, 6, 7, 8 or more electrodes 3 is used. Measurements taken from the electrodes at substantially the same time optionally include or define a set of measurements from electrodes constrained in their relative positions by a known geometry of their arrangement, or at least by the distance between them. Optionally, well-characterized movements of the probe (bending near a fixed location, axial translations of the catheter, etc.) are used as parameters indicative of bending to help to define known geometrical rearrangements among sets of measurements taken at different times.

The electrode 3 spacing is optionally at any suitable distance and may be regular or irregular among different pairs of electrodes. In some embodiments, an intrabody probe comprises a rigid section, with electrodes fixed to the rigid section at known (e.g., predetermined and/or measurable) distances from each other. In some embodiments an intrabody probe comprises multiple flexible probe segments (arranged to open to a predetermined and/or measurable spread-out configuration of inter-electrode distances, e.g., in a basket-type and/or umbrella-type configuration), each bearing a plurality of electrodes in a configuration extending therealong. Potentially, mapping from more and/or more widely distributed electrodes speeds up reconstruction, e.g., allows snapshot-type mapping of a cavity in which the probe is deployed.

Additionally or alternatively, in some embodiments, electrodes are positioned on a flexible member which can assume a curved shape (e.g., by its own predisposition to bend, under remote control, and/or in response to contact force); optionally to the extent of forming a circular and/or spiral configuration. A catheter carrying such a probe is sometimes referred to as a lasso catheter. In some lasso catheters, the electrodes are arranged in pairs, wherein the distance between electrodes within a pair is small enough to be fixed even when the catheter as a whole curves. Accordingly, some lasso catheters may include 10 electrodes that define 45 electrode pairs, among which 5 pairs are characterized by a fixed inter-electrode distance, and the inter-electrode distances in the other 40 pairs are not fixed. The relative positions of the electrodes on the flexible member are optionally calculated from knowing a control state of the flexible member, and the effect of that control state on the flexible member geometry. Optionally, electrodes of the flexible member transmit electrical signals between each other, and the level of the electrical signal is used to calculate a distance. In some embodiments, a catheter includes one or more pairs of electrodes with known intra-pair distance (i.e., known distance between the members of the pair), and unknown inter-pair distances (i.e., unknown distances between the pairs or between electrodes that belong to different pairs). In some embodiments, only two electrodes with known distance between them is included in the catheter probe. In some embodiments, the distances between some electrodes on the catheter probe are known, and the distances between some electrodes on the same catheter probe is unknown.

All these may be used in embodiments of the disclosure, as one inter-electrode distance is sufficient to provide a ruler to be used in the reconstruction as described below, although a larger number of known distances may yield a better reconstruction. A reconstruction may be identified as better than another if it provides a more useful approximation of the target than the other reconstruction. In that regard, in some embodiments, the known spacing of sensing electrodes 3 is used in voltage/spatial mapping, whereby the body cavity shape is reconstructed from voltage measurements measured by probe electrodes 3. A major principle of the reconstruction may be understood as using the structure of the intrabody probe as a kind of ruler. As this ruler is moved among multiple locations, it does not change its length. In some embodiments, possible transforms are weighted by the degree to which they keep this length constant. In embodiments where this is the only criterion for choosing a transform, the transform that keeps this length most constant is chosen to be used for the voltage/spatial mapping. Naturally, when distances between more than two electrodes are known, there are more rulers that should be fixed.

For example, in transforming each measurement made by one sensor at one instance to a corresponding location (corresponding to the location of the sensor at the instance), it is desirable that measurements taken by two sensors, spaced from each other by 2 mm (for example), are transformed to two locations, spaced from each other by 2 mm. At least, if the two measurements are transformed to locations 3 mm apart from each other, it is desirable that this distance of 3 mm is the same regardless of where the probe is. The requirement for a fixed length of the ruler may be translated to a requirement of a flexible transformation between measurement gradient and location gradient. For example, the distance between the location assigned to sensor 1 and to sensor 2 is always to be the same, even if the difference in voltages measured by sensor 1 and sensor 2 varies appreciably (for example, by a factor of 10 or more).

In some embodiments, a method of finding a transform that keeps the sister distances (i.e., distances between locations assigned to two positions of a ruler) constant comprises an optimization process. This can be understood as starting with a trial transform, estimating the degree to which rulers lengths change under this transform, and iteratively changing the transform to reduce this degree, until a minimal degree of change of rulers lengths (and/or maximal stability of rulers lengths) is achieved.

In some embodiments, the trial transform is changed iteratively not only to maximize the stability of rulers lengths, but also to satisfy one or more additional constraints in some weighted combination. In terms of the ruler concept, the ruler length is allowed to get a little longer or a little shorter in some region (and/or for some particular measurement) if that helps to produce a reconstruction which does a sufficiently better job of maintaining another constraint criterion overall. In algorithmic terms, there is a cost to increasing change of the ruler length, and a cost to increasing failure to maintain any other criteria; and the result chosen is the one that minimizes the joint cost of each. Further details regarding generating electro-anatomical images using electrodes disposed on a catheter can be found in, for example, WO 2018/120974 to Dichterman, et al., the entirety of which is hereby incorporated by reference. Further, the system 1 may be configured to obtain electrophysiological (EP) information of tissue, such as EP data related to a heart beat. EP data can be mapped onto electro-anatomical images generated by the system 1 to create electro-anatomical maps showing the propagation of EP waves, which may be useful in diagnosing arrhythmias, such as atrial fibrillation (AF). Further details related to the collection of EP data can be found in, for example, U.S. Publication No. 2018/0125575 to Schwartz, et al., the entirety of which is hereby incorporated by reference.

FIG. 1B is a schematic diagram of a processor circuit 160, according to embodiments of the present disclosure. The processor circuit 160 may be implemented in one or more of the controller 120, measurement module 120A, measurement analyzer 120B, field measurer 101B, or any other processing component shown in FIG. 1A. As shown, the processor circuit 150 may include a processor 162, a memory 164, and a communication module 168. These elements may be in direct or indirect communication with each other, for example via one or more buses.

The processor 162 may include a central processing unit (CPU), a digital signal processor (DSP), an ASIC, a controller, an FPGA, another hardware device, a firmware device, or any combination thereof configured to perform the operations described herein. The processor 162 may also be implemented as a combination of computing devices, e.g., a combination of a DSP and a microprocessor, a plurality of microprocessors, one or more microprocessors in conjunction with a DSP core, or any other such configuration.

The memory 164 may include a cache memory (e.g., a cache memory of the processor 162), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 164 includes a non-transitory computer-readable medium. The memory 164 may store instructions 166. The instructions 166 may include instructions that, when executed by the processor 162, cause the processor 162 to perform the operations described herein with reference to FIG. 1A. Instructions 166 may also be referred to as code. The terms “instructions” and “code” should be interpreted broadly to include any type of computer-readable statement(s). For example, the terms instructions and code may refer to one or more programs, routines, sub-routines, functions, procedures, etc. Instructions and code may include a single computer-readable statement or many computer-readable statements.

The communication module 168 can include any electronic circuitry and/or logic circuitry to facilitate direct or indirect communication of data between the processor circuit 160, the catheter electrodes 103, skin patch electrodes 105, field measurer 101B, or any other suitable system component. In that regard, the communication module 168 can be an input/output (I/O) device. In some instances, the communication module 168 facilitates direct or indirect communication between various elements of the processor circuit 160 and/or the system 1 (FIG. 1A).

Figure 2:
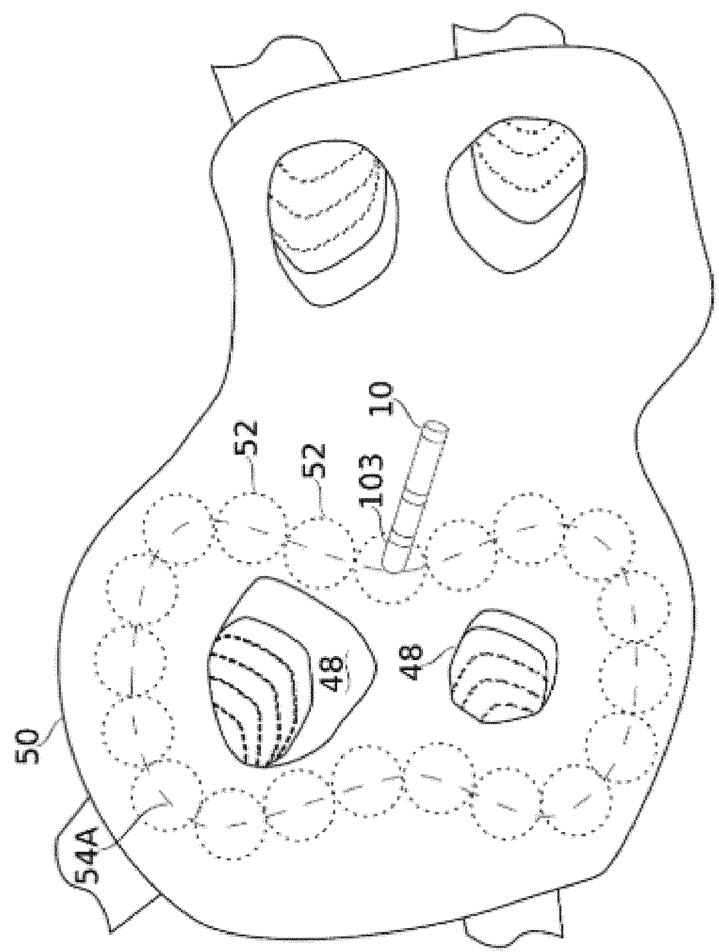
FIG. 2 is a perspective view of an inner wall of a left atrium during an ablation procedure, according to aspects of the present disclosure.

FIG. 2 is a flattened view of an inner wall 50 of a left atrium during an ablation treatment procedure performed using a catheter 10 carrying a treatment electrode 103, according to some embodiments of the present disclosure. In particular, FIG. 2 shows an inner wall 50 of a left atrium, which includes pulmonary vein openings 48 or ostia of the right superior and inferior pulmonary veins, and the left superior and inferior pulmonary veins. The ablation procedure is carried out by placing the electrode 103 against the tissue and applying a voltage or electrical current for a period of time sufficient to create an ablation point 52 or lesion of a given radius and depth. However, it will be understood that other types of ablation or therapy can be used, such as radio frequency ablation, cryoablation, thermal ablation, ultrasound ablation (such as high frequency ultrasound ablation), or any other suitable type of therapy. In that regard, the catheter 10 can include components and be structurally arranged and configured to perform any of these types of therapy, or any other suitable type of therapy. By creating many ablation points 52 along an ablation line 54A, with the ablation points 52 sufficiently close to one another, an electrically isolating wall can be created to block arrhythmia-causing electrical signals. For example, in some embodiments, between about 60 and about 90 ablation points 52 are created to form the line 54A or loop around the area of tissue. Each ablation point 52 may be formed by ablating the tissue for between about 30 and about 90 seconds to create an electrically isolating lesion.

Although ablation is generally described herein with respect to ablation of an atrial wall for the treatment of atrial fibrillation, it should be understood that the descriptions also apply, changed as necessary, to the planning of ablation in other tissues; for example: neural tissue, tumor tissue (for example, cancer), other abnormal growth tissue such as warts, skin tissue, mucous membrane, or another tissue.

In order to adequately block undesired electrical pulses or signals that cause arrhythmia, it is desirable that the ablation points 52 be sufficiently close to one another to create a closed loop. However, while it may appear to a physician that an adequate ablation line 54A has been created at the time of the ablation procedure, the remodeling of the heart can cause the ablation points 52 to migrate and drift apart, creating gaps in the ablation line that can lead to the return of atrial fibrillation.

Figure 3B:
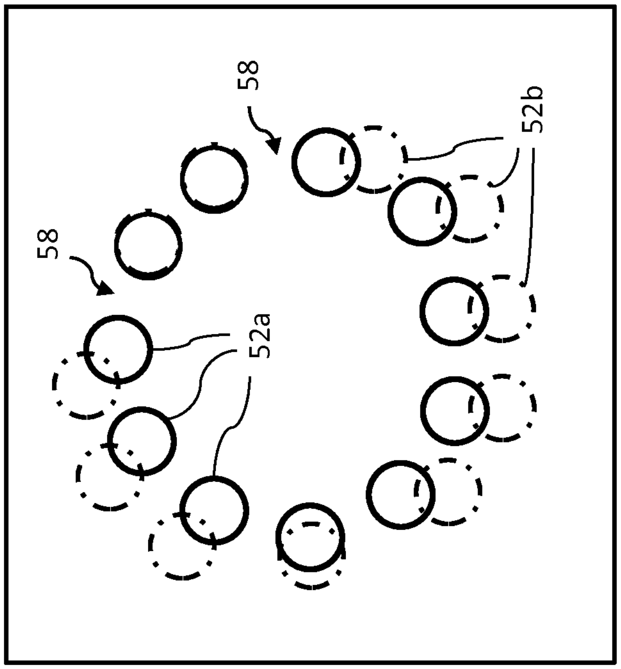
FIG. 3B is a diagrammatic view of the locations of the plurality of ablation points after the tissue has remodeled, relative to the locations of the plurality of ablation points before the tissue remodeled, according to aspects of the present disclosure.
Figure 3A:
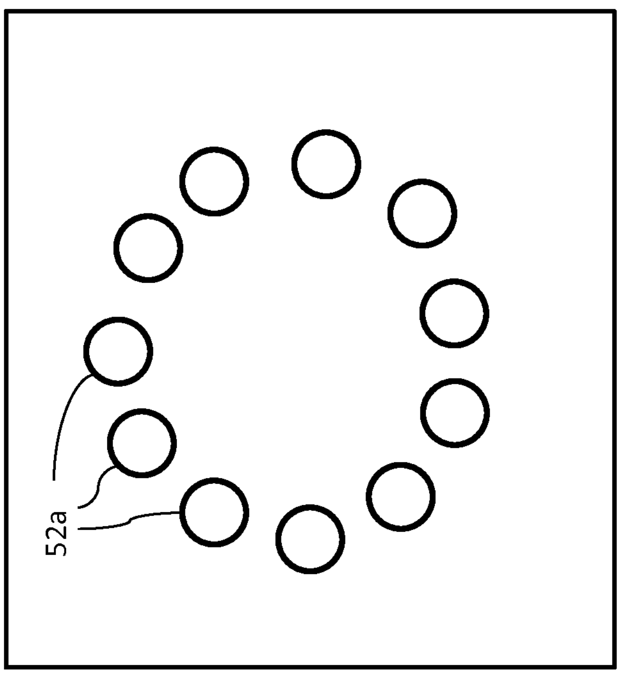
FIG. 3A is a diagrammatic view of the locations of a plurality of ablation points in a tissue before the tissue has remodeled, according to aspects of the present disclosure.

FIGS. 3A and 3B illustrate the migration of ablation points 52 relative to anatomical landmarks and/or other ablation points as a result of remodeling of the heart. As described above, treatments such as ablation can quickly result in the return of the heart to a normal sinus rhythm (NSR), even during the treatment procedure. As the heart returns to the NSR, the size of some anatomical features of the heart, such as the atria, can contract and/or undergo other geometrical changes. The change in geometry is referred to as remodeling. In some instances, the atria can remodel in as soon as three heartbeats after a successful lesioning. Once the heart has remodeled, the tagged locations of the ablation points or treatment locations (e.g., ablation points 52, FIGS. 2, 3A) may no longer be valid. In that regard, FIG. 3A illustrates an arrangement of ablation points 52*a* on an atrial wall before the heart has remodeled. FIG. 3B illustrates an arrangement of the ablation points 52*b* after the heart has remodeled. As shown in FIG. 3B, the re-arrangement or migration of the ablation points 52 has created gaps 58 between the ablation points 52, which can allow for arrhythmia-inducing circuits to reform and escape. These gaps may result from a looser arrangement of the ablation points 52*b* in the remodeled heart.

Accordingly, it is often necessary to perform a re-do or re-study procedure to correct the ablation line after the heart has remodeled. Because the heart can remodel quickly, a re-study may be required even while the original treatment procedure is still underway. In other instances, a re-study may be required weeks, months, or years after the original treatment procedure. Conventional re-study procedures may involve a complex process of pacing, which can be time-consuming and unprecise. The present disclosure describes devices, systems, and associated methods that co-register a first image or map of an anatomy, including tagged treatment locations, and a second post-procedure image or map of the anatomy using a non-rigid transformation. The co-registration is used to map the treatment locations tagged on the first image to the second image to identify areas that are more likely to allow for escape of arrhythmia-inducing electrical signals.

A major challenge in carrying out these embodiments is finding a transform that brings points from one image to another in an anatomically meaningful manner despite of the remodeling of the heart. That is, the registration should register points of a certain anatomical designation in a first image to anatomically corresponding points in the second image. The anatomically corresponding points are points of the same certain anatomical designation in the second image. For example, the registration should register points in the blood pool in the first image to points in the blood pool in the second image, points at the wall of the first image to points at the wall of the second image, points in a given landmark in the first image to points in the same landmark in the second image, etc. Examples of landmarks may include: the fossa ovalis (FO), any one of the pulmonary veins or an ostium thereof, any one of the vena cava, any cardiac valve, etc.

Figure 4:
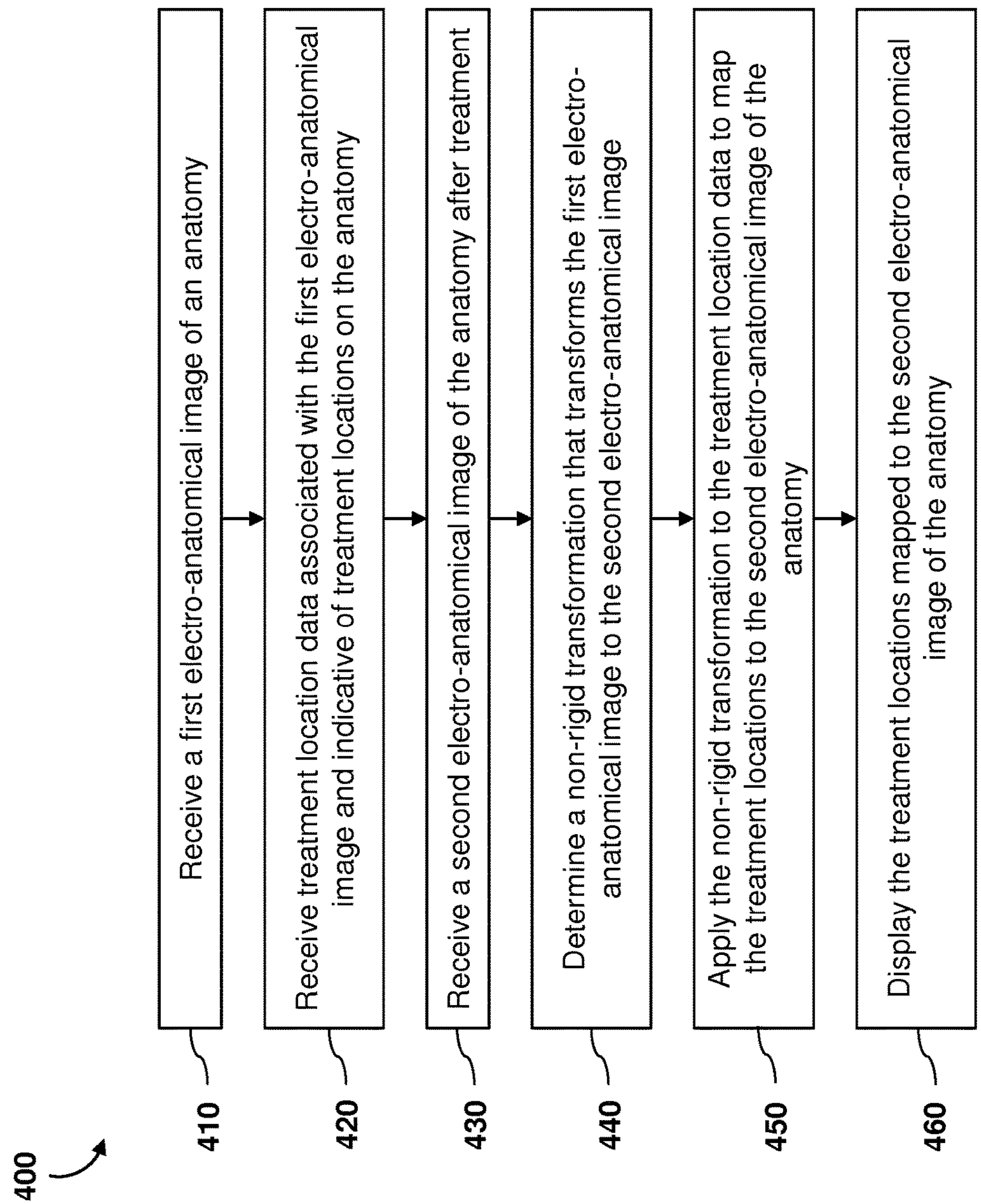
FIG. 4 is a flow diagram of a method for co-registering electro-anatomical images, according to aspects of the present disclosure.

FIG. 4 is a flow diagram illustrating a method for co-registration of electro-anatomical images, according to an embodiment of the present disclosure. It will be understood that one or more of the steps of the method 400 can be performed using the system 1 shown in FIGS. 1A-1B, or components of the system 1, including the controller processing system 20, the EM field measurer 10, catheter 11, skin patch electrodes 5, and any other suitable components. In step 410, the system receives a first electro-anatomical image of an anatomy, such as a heart. The electro-anatomical image may be obtained using a plurality of electrodes on a catheter positioned within the patient's anatomy to measure electrical fields induced by a plurality of patch electrodes placed on the patient's skin. As discussed above, the catheter can include 2, 3, 4, 5, or more electrodes. Based on the measured voltages at two or more of the electrodes and the known spacing between the electrodes, the system converts the measured voltages and/or electrical signals into geometrical measurements of the anatomy (e.g., distance measurements). The catheter is moved around the inside of the anatomy and to various features therein to obtain electro-anatomical data or measurements used by the system to create the electro-anatomical image.

For example, in one embodiment, the anatomy comprises the left atrium, and the catheter is moved to various locations within the left atrium and its peripheral locations and features, such as the left atrial appendage, the left superior and inferior pulmonary veins, the right superior and inferior pulmonary veins, and/or the mitral valve. In some embodiments, the electro-anatomical image or image data is received directly from the electrodes of the catheter. In other embodiments, the electro-anatomical image is received from a memory component. For example, in some embodiments, the first electro-anatomical image is used in co-registration several weeks or months after the first electro-anatomical image was obtained.

In step 420, the system 100 receives treatment location data associated with the first electro-anatomical image and indicative of treatment locations on the anatomy. In that regard, during a treatment procedure, such as ablation, two or more electrodes on the catheter may be obtaining electro-anatomical image data or positioning data while a treatment electrode is performing the ablation. The determined location of the catheter or treatment location with respect to the first electro-anatomical image is tagged on the first electro-anatomical image. In some embodiments, the treatment location data indicates the treatment locations (e.g., ablation points, ablation lines) in cartesian, Euclidian, polar, or other suitable coordinate systems. In some embodiments, the treatment location data indicates the treatment locations relative to a catheter track, as further described below. In some embodiments, the treatment locations are tagged relative to one or more anatomical landmarks, such as an ostium of a pulmonary vein.

In step 430, the system 100 receives a second electro-anatomical image of the anatomy after treatment. In some instances, the second electro-anatomical image of the anatomy may represent a heart after undergoing remodeling precipitated by the treatment procedure. In that regard, in some instances, the heart shown in the second electro-anatomical image may differ geometrically from the heart shown in the first electro-anatomical image, such as by volume, relative positions of anatomical landmarks, wall size, etc. However, in some aspects, one or more anatomical landmarks or features in the heart may remain substantially unchanged, such as the size of the ostia or openings of the pulmonary veins, the relative spacing between superior and inferior pulmonary veins, etc.

In some embodiments, the second electro-anatomical image is received shortly after or during a treatment procedure. In some embodiments, the second electro-anatomical image is received several days, weeks, or months after the treatment procedure. In some embodiments, the first and second electro-anatomical images are obtained using the same system. In other embodiments, the first and second electro-anatomical images are obtained using different systems.

In step 440, the system determines a non-rigid transformation between the first electro-anatomical image and the second electro-anatomical image. A non-rigid transformation may include transformations other than scaling, translation, rotation, compression, or expansion. In that regard, as described above, the remodeling of the heart may result in some features of the heart, such as the atrial wall or volume of the atrium, getting larger or smaller while other features remain substantially unchanged, or are less affected by remodeling. Accordingly, the transformation may allow for various points in the first electro-anatomical image to be mapped onto locations in the second electro-anatomical image that are representative of the remodeling of the heart.

For example, in some embodiments, the transform is based on a probabilistic correspondence model that assigns a probability to any correspondence between a point in one image (e.g., the image of the original heart) and each point in the other image (e.g., the image of the remodeled heart). The probability may be assigned so that points near to each other in one image have a larger probability to correspond to points near each other in the other image than to correspond to points far away from each other in the other image. Such a condition for assigning probabilities may be referred to herein as a coherence condition. A coherence condition may facilitate the anatomical meaningfulness of the correspondence between points in the two images, because points of a given landmark are usually nearby each other more than to points of other landmarks, and this is generally true for each of the two images.

In one way of applying a coherence condition, the probability may be found by minimizing a cost function that depends on the sum of differences between points in one image and distances between corresponding points in the other image. Additionally or alternatively, the probabilistic model may assign higher probability to transformations that minimize the distance that the points move from one image to the other (assuming, for example, that the origins of the two images are at the same point). In some embodiments of the disclosure, the probabilistic model maximizes the coherency between tracks leading from points in one image to corresponding points in the other image, for example, a coherent point drift model. In some embodiments, the points may be points of the images In some embodiments, each of the images is generated based on electrical measurements (e.g., voltage and/or impedance measurements) taken by a plurality of electrodes mounted on a rigid portion of a catheter. In such embodiments, the points of each image are interconnected in groups, for example, if an image was acquired with a catheter carrying four electrodes, the image is made of quartets of points, where the distance between the points in a group (e.g., in a quartet) correspond to the distance between the electrodes. In some such embodiments, the transform is generated to respect the known distances between the electrodes that acquired the electrical readings. A condition to respect the known distances is referred to herein as local scaling condition. For example, the transform may be made to prefer correspondence models in which the distances between points within a group in one image is the same as the distances between points within a corresponding group in the other image. Similarly, in some embodiments, the transform may be made to prefer correspondence models in which ratios between the distances between points within a group in one image is the same as the ratios between the distances between points within a corresponding group in the other image.

In some embodiments of the disclosure, the coherence constraints are added to constraints on relative positions assigned to sensors (e.g., electrode positions). For example: two points at nearby regions in one image are assumed to correspond to points which are also nearby under some metric. In some embodiments, points belonging to the same group may be referred to as sister points occupying sister locations, and the distances between sister locations may be referred to as sister distances. A coherence criterion may be set to require that sister distances change smoothly across the images. An algorithm for finding a transformation that generates smooth changes in sister distances may be obtained, for example, when the spatial distribution of sister distances is decomposable to components having different spatial frequencies. The algorithm then may penalize transformations generating sister-distance-distribution of high frequency components, and the overall penalty may be minimized (by reducing the contribution of high frequency components to the distribution of sister distances) in order to find a coherent transformation. For example, a penalty may be set to each component, and the penalty may increase as the frequency of the component increases. This way, distributions that include only low frequency components would nearly not be penalized, and those that include components of very high frequencies will be penalized heavily. A minimization procedure may be applied to minimize the penalty, to find a transformation that results in sister distances that change smoothly (i.e., with mainly small frequency components), which is an example of a coherence criterion.

In some embodiments, the registration transform may be found by optimizing the transform of one entire image to another. In other embodiments, the registration transform may be found by optimizing the transform of only selected points of the first image (or point-cloud) to selected points in the second image (or point-cloud).

Figure 5B:
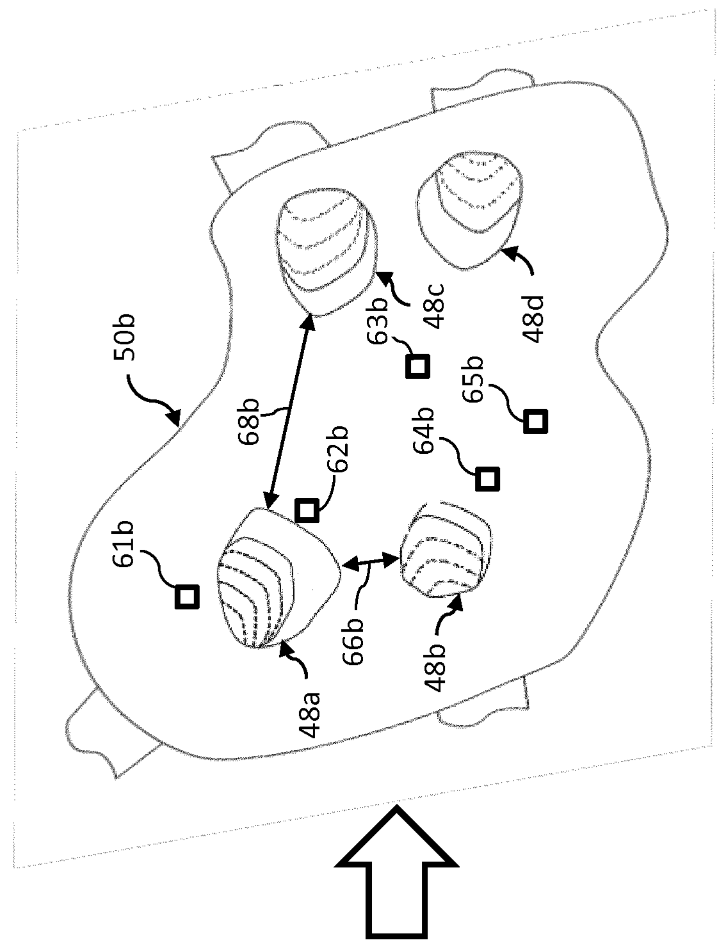
FIG. 5B is a perspective view of an inner wall of the left atrium shown in FIG. 5A shown after the heart remodels, according to aspects of the present disclosure.
Figure 5A:
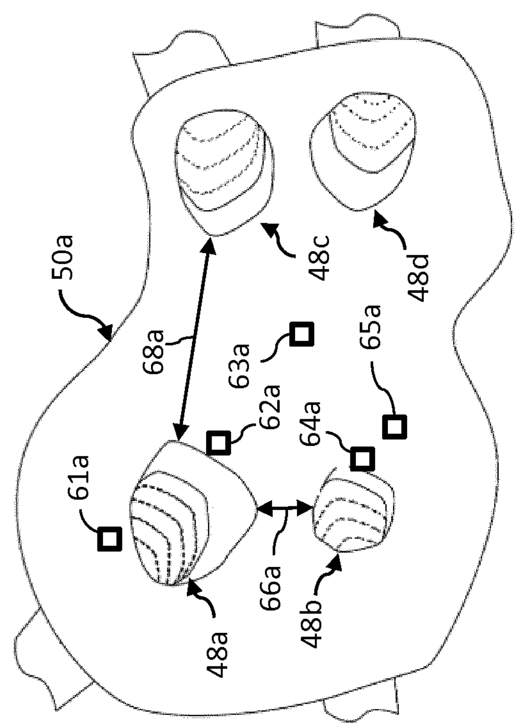
FIG. 5A is a perspective view of an inner wall of a left atrium before the heart remodels, according to aspects of the present disclosure.
Figure 6:
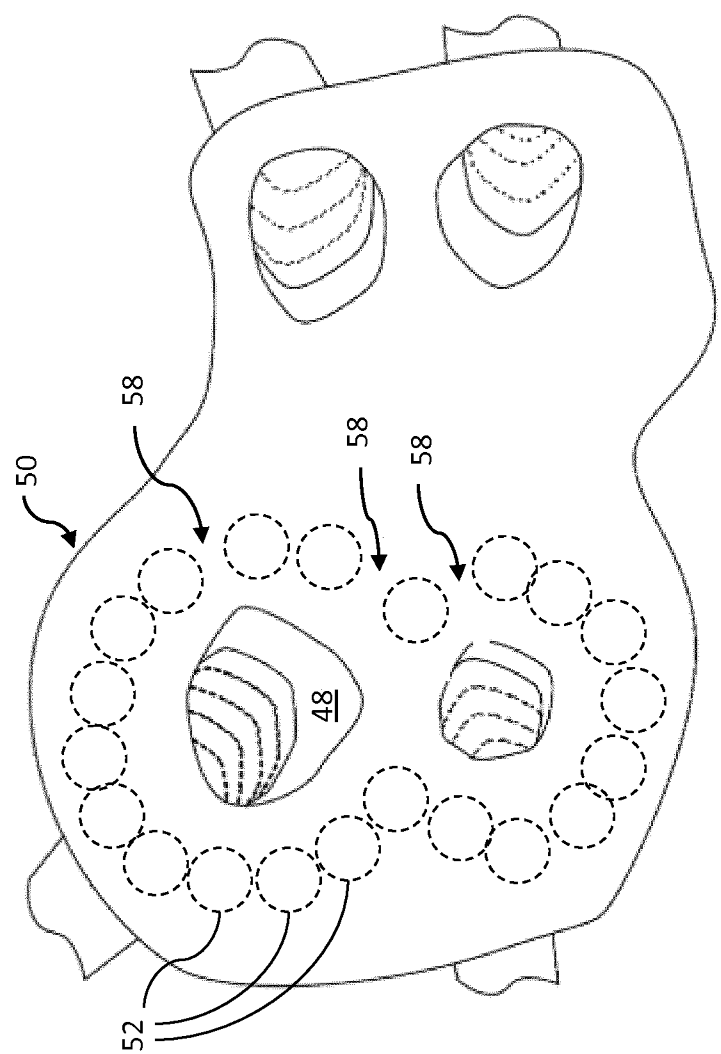
FIG. 6 illustrates an interface showing an electro-anatomical image of the left atrium generated after an ablation procedure, with a plurality of ablation points registered onto the electro-anatomical image, according to aspects of the present disclosure.

An example of the electro-anatomical imaging and transformations of the method 400 are shown in FIGS. 5A, 5B, and 6. FIG. 5A shows a first electro-anatomical image of a left atrium, that includes openings to pulmonary veins 48*a-d*, and the atrial wall 50*a*. A plurality of reference points 61*a*, 62*a*, 63*a*, 64*a*, 65*a* are shown at various locations on the atrial wall 50*a*. FIG. 5B shows a second electro-anatomical image of the left atrium after the heart has remodeled as a result of a treatment procedure. In that regard, the size and shape of the atrial wall 50*b*, as well as the relative locations of the points 61*b*, 62*b*, 63*b*, 64*b*, 65*b* have changed. However, some features, such as the size and/or shape of the pulmonary vein openings 48*a-d*, as well as the relative spacing between superior and inferior pulmonary vein openings 66*a*, 66*b*, are similar or substantially unchanged between the first and second electro-anatomical images. For example, the size of pulmonary vein openings 48*a* and 48*b* may remain substantially constant between the two images, as well as relative position/distance between them. However, the distances 68*a*, 68*b* between pulmonary vein opening 48*a* and 48*c* may differ between the two images. Thus, the remodeling of the heart has led to a non-rigid or non-homogenous migration of tissue. In that regard, in some embodiments, points near to certain anatomical landmarks, such as points 61*a*, 62*a*, and 64*a*, may exhibit less movement between images, while other points on the atrial wall, such as 63*a* and 65*a* may exhibit greater movement between images to reflect the non-uniform changing geometry of the heart.

As mentioned above, the mapping and registration illustrated in FIGS. 5A and 5B can be used to create updated electro-anatomical images or maps that show the rearrangement of treatment locations (e.g., ablation points) resulting from the remodeling of the anatomy. FIG. 6 shows a reconstructed electro-anatomical image of the left atrium with ablation points from a first electro-anatomical image mapped onto a second electro-anatomical image. The image shown in FIG. 6 can be part of a user interface shown on a display device of the system 100. As compared with the positions shown in FIG. 2, the locations of the ablation points 52 have moved as a result of the remodeling of the heart such that gaps 58 have developed between some of the ablation points. By mapping the ablation points 52 using the transformation described above, the gaps 58 can be displayed and identified so that a physician can more readily plan and execute a re-do procedure to fill in the gaps 58 to help the heart return to NSR. The reconstructed image with the mapped treatment locations shown in FIG. 6 can be shown along with an indicator of a catheter or treatment device to guide the operator during the re-do treatment procedure.

The present disclosure contemplates several specific processes and algorithms to determine and apply the transformations discussed above. In that regard, FIGS. 7 to 18 illustrate various methods and approaches for non-rigid transformations used in the co-registration of electro-anatomical images.

Figure 7:
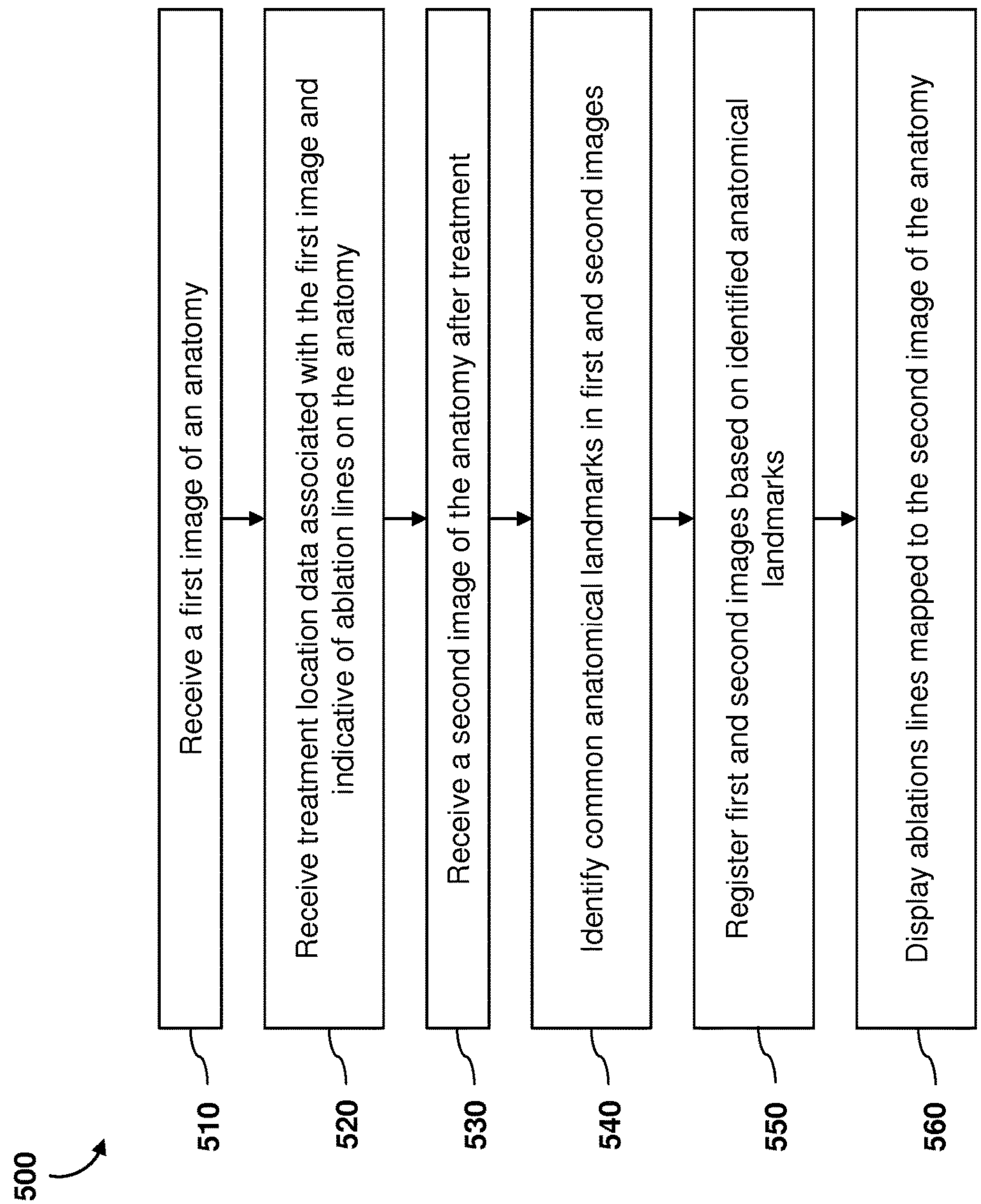
FIG. 7 is a flow diagram illustrating a method for co-registering electro-anatomical images based on common identified landmarks, according to aspects of the present disclosure.
Figures 8A, 8B:
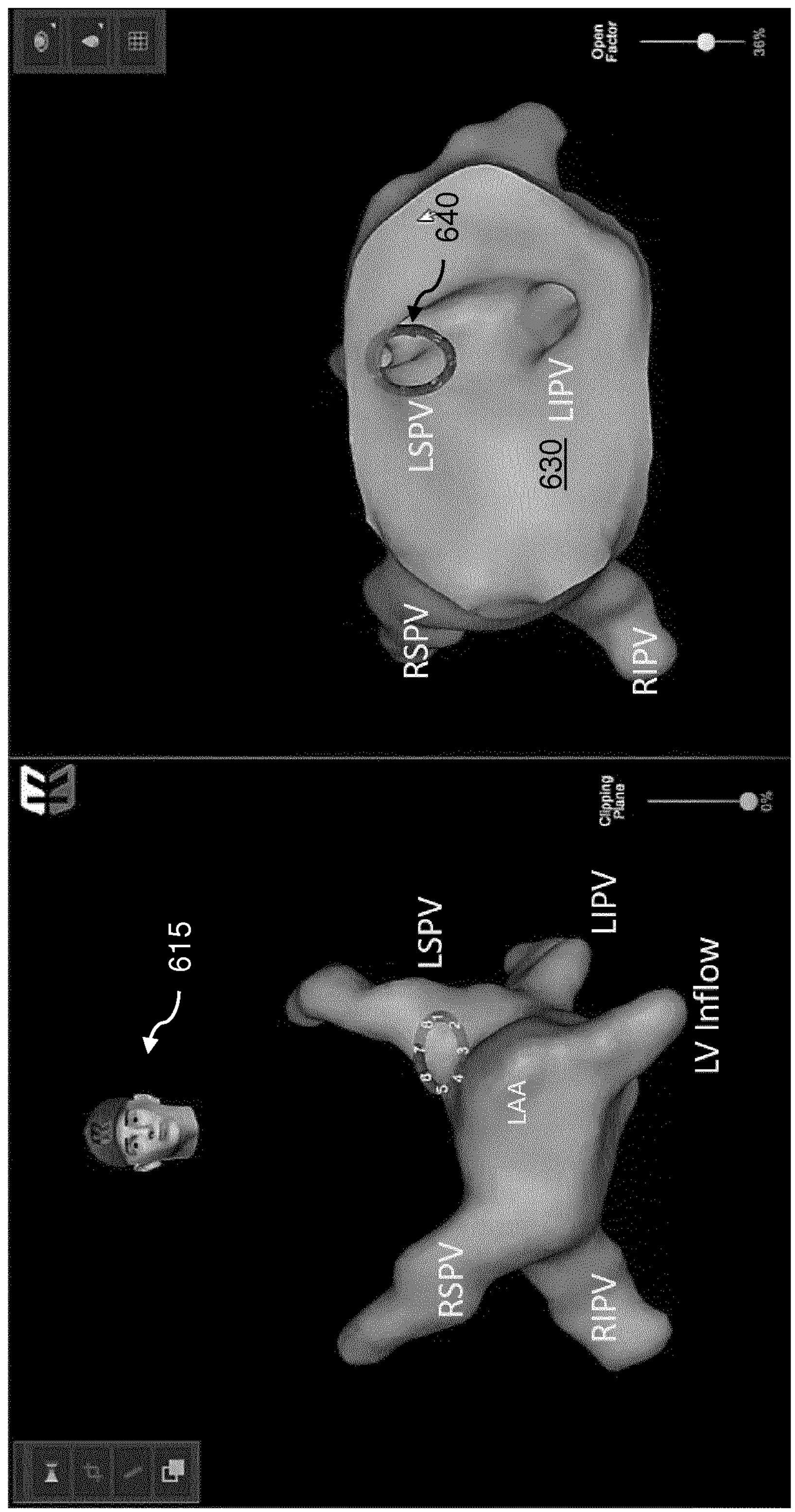
FIG. 8A is an external perspective view of an electro-anatomical image of a left atrium, according to aspects of the present disclosure.
FIG. 8B is cutaway view of an electro-anatomical image of a left atrium, according to aspects of the present disclosure.

FIG. 7 is a flow diagram illustrating a method 500 for co-registering first and second images using identified common landmarks in the first and second images. As in the method 400, the images in the method 500 can comprise electro-anatomical images of a heart, in some embodiments. In step 510, the system receives the first electro-anatomical image of the anatomy, which may include a feature of a heart, such as a left atrium. In step 520, the system receives treatment location data that is tagged in, or otherwise associated with the first image. The treatment location data indicates ablation lines and/or points where ablation was applied in the first image (e.g., ablation points). In step 530 the system receives a second image after at least part of the treatment has been applied. As described above, the anatomy in the second image may exhibit different geometrical characteristics as a result of remodeling when compared to the first image. In step 540, common anatomical landmarks are identified in the first and second images. In some embodiments, landmarks are first identified in the first image before or during a treatment procedure. The same landmarks are then identified in the second image to determine the transformation. For example, referring to FIGS. 5A and 5B, a user may identify the locations of one or more pulmonary vein openings 48 in the first image, and identify the locations of the same pulmonary vein openings in the second image.

In some embodiments, the landmarks are identified by an operator via a user input device. For example, the operator can identify the location of a landmark in the first image shown on a display using one or more of a mouse, joystick, keyboard, track ball, or touch screen device. In some embodiments, the user input used to identify the landmark may include selecting one or more points on or near the landmark. In some embodiments, the user input may include tracing around a perimeter of the landmark. In some embodiments, the user input may include overlaying and/or resizing a shape or object on the display of the image that represents the shape or profile of the landmark.

In step 550, the system registers the first and second images based on the identified anatomical landmarks. In some embodiments, step 550 comprises determining a transformation between the first and second images that uses the common identified landmarks of the first and second images as input. For example, the transformation may include aligning or co-registering points or areas of the first and second images associated with the common identified landmarks and transforming the remaining points or areas of the image using one or more non-rigid transformation techniques described above. In step 560, the ablation lines and/or points are mapped to the second image based on the common anatomical landmarks and the transformation.

Figure 9:
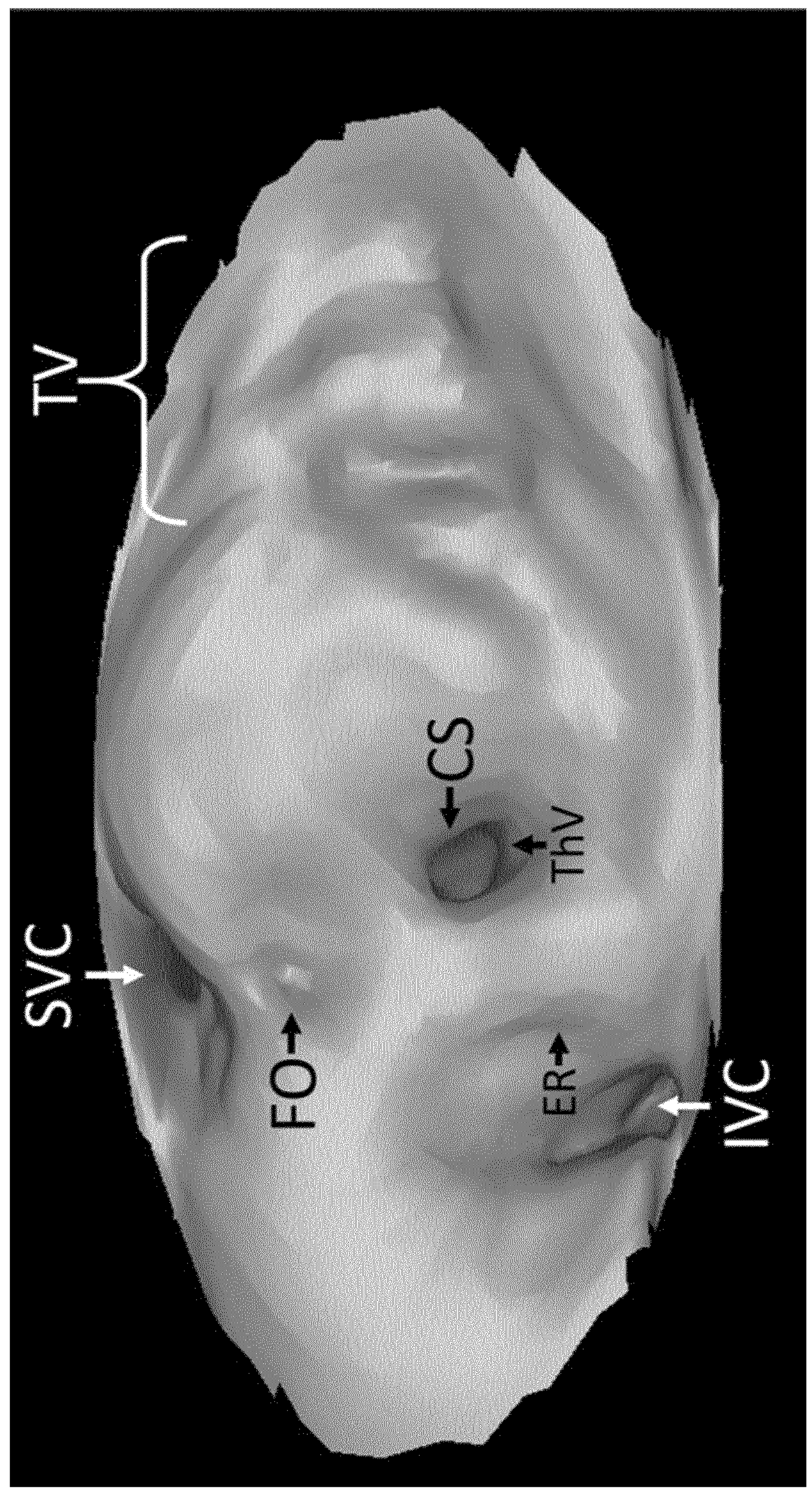
FIG. 9 is a perspective view of an electro-anatomical image of an interior surface of a heart, according to aspects of the present disclosure.
Figure 10:
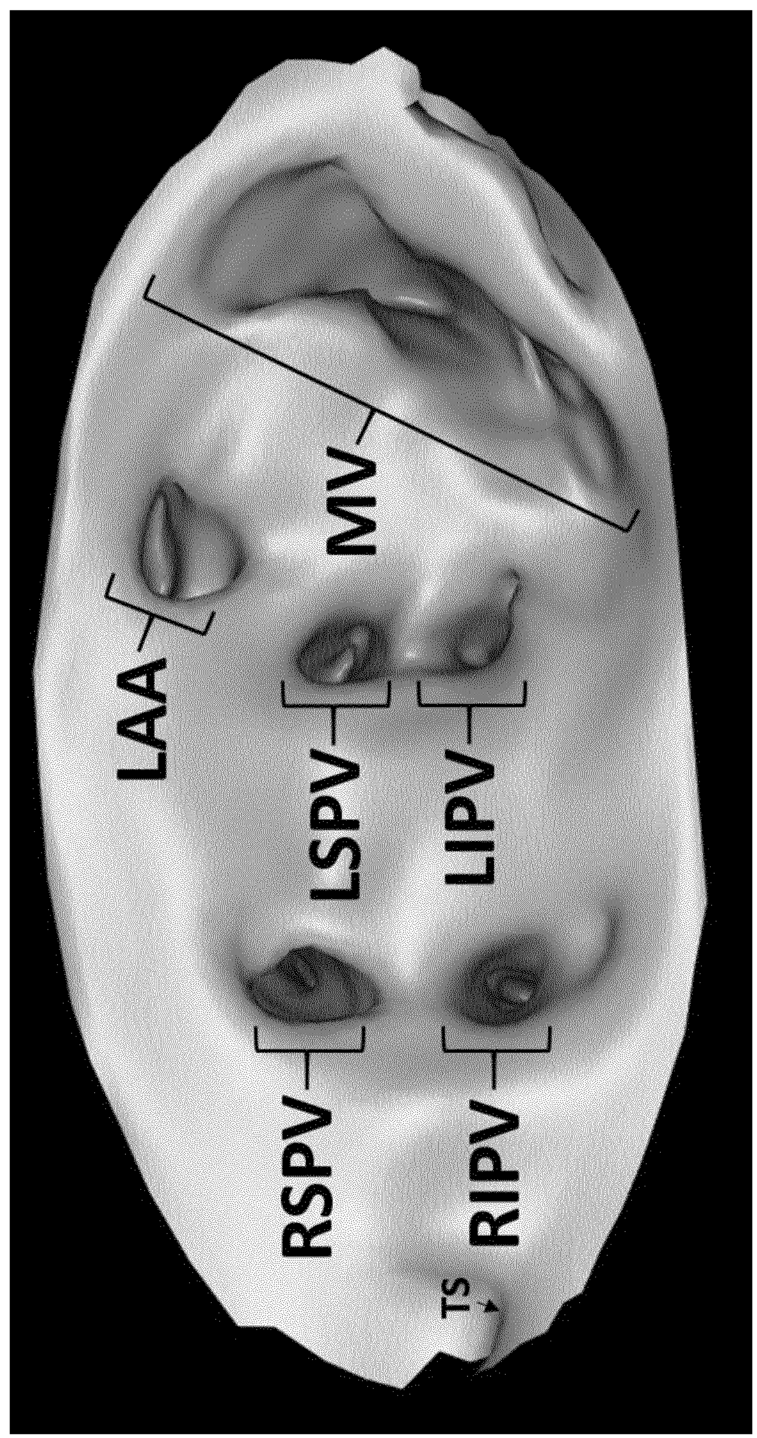
FIG. 10 is a perspective view of an interior wall of an electro-anatomical image of a left atrium, according to aspects of the present disclosure.
Figure 11:
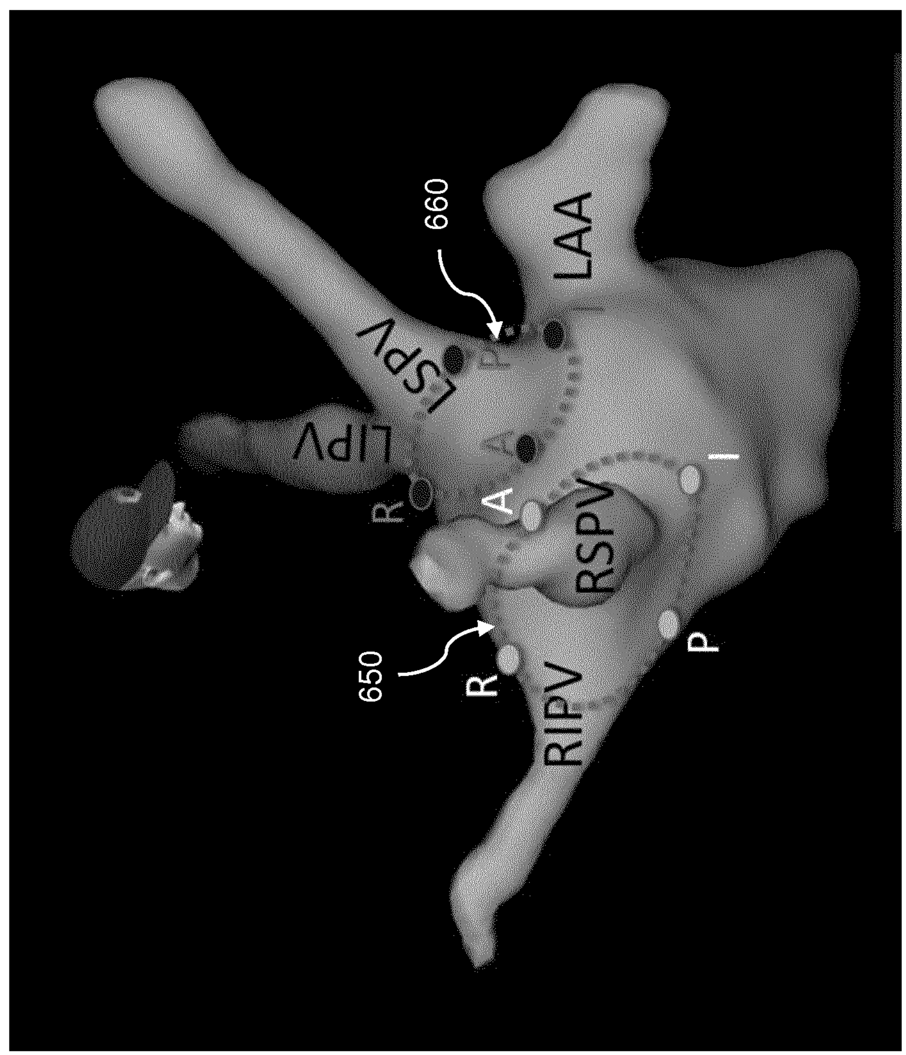
FIG. 11 is an external perspective view of an electro-anatomical image of a left atrium with ablation lines overlaid on the electro-anatomical image, according to aspects of the present disclosure.

FIGS. 8-11 illustrate various interfaces and views of electro-anatomical images of the heart, according to some embodiments of the present disclosure. In some embodiments, the views shown in FIGS. 8-11 can be used to identify landmarks, plan treatments, and guide treatments using electro-anatomical images. FIG. 8A shows a perspective view of an electro-anatomical image of a left atrium, including the right superior and inferior pulmonary veins (RSPV, ISPV), the left superior and inferior pulmonary veins (LSPV, LIPV), left ventricle inflow (LF inflow), and left arterial appendage (LAA). In particular, FIG. 8A is a perspective view of the left atrium, and includes an orientation indicator 615 that indicates to a user the orientation of the view relative to the patient's anatomy. FIG. 8B is a partial cut-away view of the electro-anatomical image shown in FIG. 8A, with an inner atrial wall 630 revealed to show the openings of the left superior and inferior pulmonary veins, which is a location that may be of particular interest for AF treatment planning FIG. 8B also shows ablation line 640 overlaid on the interior atrial wall 630. In that regard, the ablation line 640 may represent the ablation line tagged or indicated on a first electro-anatomical image before, during, or after treatment, and before the heart has remodeled as a result of ablation treatment. In other embodiments, the ablation line 640 may represent the ablation line as mapped onto a second electro-anatomical image that was obtained after the heart remodeled. Other views can also be advantageous for treatment planning and guidance. For example, FIG. 9 shows a flattened panoramic view of an interior wall of a left atrium, which shows openings of the superior and inferior vena cava, fossa ovalis (FO), tricuspid valve (TV), Triangle of Koch, Tendon of Todaro, coronary sinus (CS), coronary sinus valve (ThV), and inferior vena cava valve (ER). FIG. 10 is a similar flattened panoramic view of the left atrium which shows the openings of the right superior and inferior pulmonary veins (RSPV, ISPV), the left superior and inferior pulmonary veins (LSPV, LIPV), the left atrial appendage (LAA), and the mitral valve (MV). FIG. 11 shows an external, three-dimensional perspective view of the features of the left atrium with ablation lines 650, 660 overlaid on the corresponding portions of the image. In that regard, FIG. 11 may represent a first electro-anatomical image with tagged treatment locations, or a co-registered electro-anatomical image showing the transformed or co-registered locations of the ablation lines on a second electro-anatomical image. It will be understood that any of the landmarks identified in FIGS. 8-11 can be used to determine a transformation according to the method 500. Further, any of the landmarks identified in FIGS. 8-11 may be targeted for treatment as described above.

Figure 12:
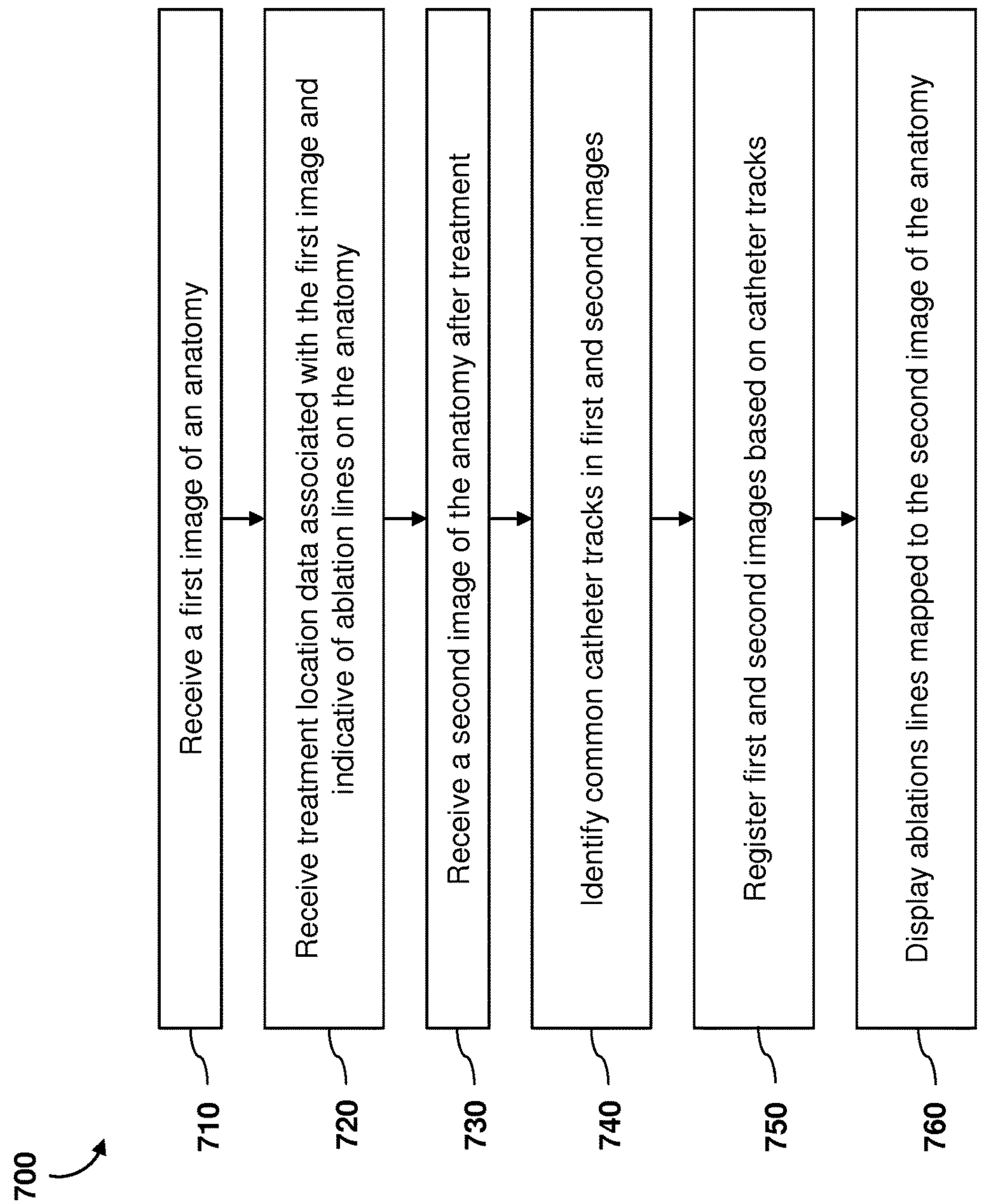
FIG. 12 is a flow diagram illustrating a method for co-registering electro-anatomical images based on common catheter tracks, according to aspects of the present disclosure.

FIG. 12 is a flow diagram illustrating a method for co-registering first and second images using common catheter tracks used in creating the first and second images. In particular, the catheter tracks can be described as the paths traveled by a sensing catheter comprising a plurality of electrodes in obtaining electro-anatomical data used to generate a respective electro-anatomical image. In some embodiments, the sensing catheter may be advanced to a distal position, and slowly drawn proximally across the catheter track (i.e. pullback). In some instances, an operator may use or select the same or similar catheter tracks to generate the first and second images. Accordingly, a correspondence between electro-anatomical data measurements obtained at the same or similar locations along the same or similar catheter tracks between the first and second images can be used to determine the transformation of the first image to the second image, and thereby to map treatment locations (e.g., ablation lines) tagged on the first image to the second image.

Similar to the method 400 and 500, in step 710, the system receives a first image of an anatomy. The first image may have been acquired by obtaining electro-anatomical data or measurements along a catheter track using a sensing catheter, as described above. Accordingly, in some embodiments, the electro-anatomical image data points are associated with a location along the catheter track of the sensing catheter, or with the location of one or more electrodes of the sensing catheter, at which the particular electro-anatomical image data points were obtained. The corresponding locations of the catheter and/or electrode(s) can be saved to memory along with the electro-anatomical data points. In step 720, the system also receives treatment location data that indicates, with respect to the first image, the locations of ablation lines or points, or other treatment locations on the anatomy. In step 730, the system receives a second image of the anatomy. The second image may have also been acquired by obtaining electro-anatomical data or measurements along a catheter track using the same catheter or a different catheter, such that the electro-anatomical image data points of the second image are also associated with a catheter track. In step 740, common catheter tracks are identified in the first and second images to find a correspondence between the data points of the first and second images. For example, in some embodiments, the physician(s) carrying out the imaging procedure may guide the catheter along predetermined tracks in the patient's heart, and mark (e.g., by the user interface 40), when the catheter goes along each of these tracks, so there is a record of beginning and end of each track, and all points visited along the track. The predetermined tracks may be well-defined in terms of the heart anatomy. For example, in treating the left atrium, the predetermined tracks may include four tracks, each going from the point of entrance into the left atrium (e.g., the fossa ovalis) to one of the pulmonary veins. The number of these tracks may differ from four, for example, if the anatomy of the patient includes less or more pulmonary veins. A fifth track may go from the entrance point to the mitral valve. Additional examples of tracks may include tracks from the entrance point to well-defined landmarks, such as the left atrial appendage and mitral valve aperture. Exemplary tracks are further described below with respect to FIGS. 13-16.

In step 750, the non-rigid transformation is applied to the first electro-anatomical image data, in particular the treatment location data, to map the treatment locations originally tagged on the first electro-anatomical image to the second electro-anatomical image. In step 760, a display device of the system or in communication with the system shows the treatment locations mapped onto the second electro-anatomical image to indicate areas where additional ablation points or lines should be performed.

Figure 13:
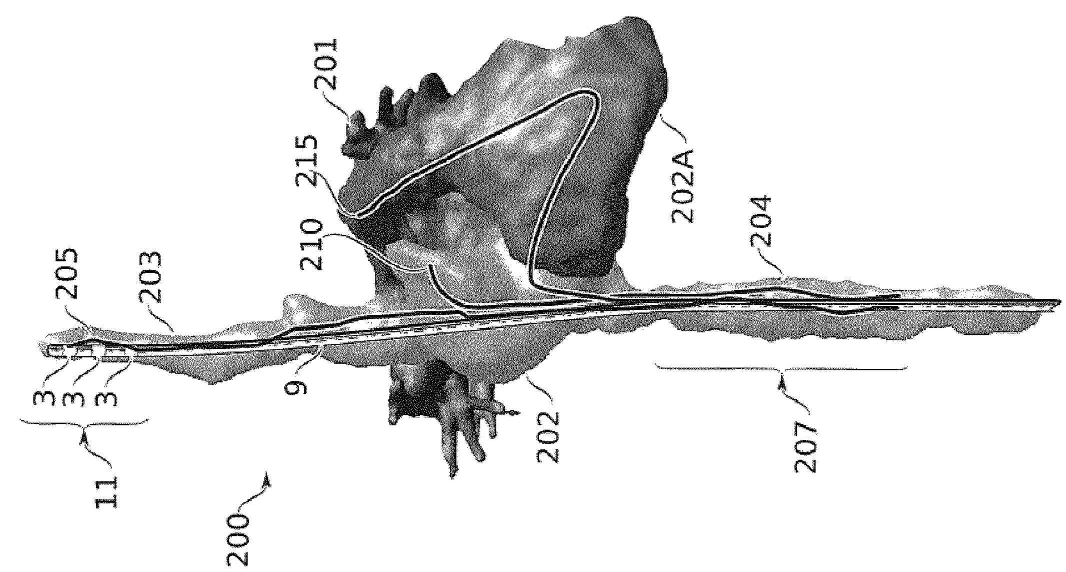
FIG. 13 is a perspective view of catheter tracks within an electro-anatomical image of a heart, according to aspects of the present disclosure.

FIGS. 13-16 illustrate a plurality of catheter tracks which may be used to obtain electro-anatomical images, and to co-register the electro-anatomical images based on the catheter tracks, as described with respect to the method 700. In particular, FIG. 13 schematically represents the courses of some pre-determined catheter tracks 205, 210, 215 through regions of the right ventricle 202A, right atrium 202, superior vena cava 203, and inferior vena cava 204 of a heart 200, according to some embodiments of the present disclosure. Also indicated is the left atrium 201. As mentioned above, the catheter tracks can be described as the paths of movement of the electrodes of the catheter within the heart chambers and/or blood pool while the catheter is obtaining electro-anatomical data. Physicians may use any of a number of pre-determined catheter tracks that are characterized by specific features or regions of the anatomy, such as the ostia of veins, valves, atria, or other regions. In particular, the paths may be defined by pre-determined starting and stopping points associated with features or regions of the anatomy. The catheter tracks may be well-defined or understood such that they can be repeated by physicians at various times before, during, or after a treatment procedure. As described above with respect to the method 700, by repeating a same catheter track to generate different electro-anatomical images, the different electro-anatomical images can be co-registered based on the common catheter track.

Catheter tracks 205, 210, 215 comprise examples of how a catheter probe 11 may be moved through atrial chambers of a heart in order to quickly register an image of a remodeled heart to an image of an original heart. Roughly, the tracks also correspond to catheter configuration before pullback (an example of a catheter 9 with probe 11 comprising three electrodes 3 is shown in a position poised for pullback along track 205), since pullback is in the direction back along the length of the catheter. The correspondence is not perfect, due, for example, to oscillations of the free catheter end, effects of catheter mechanical properties, etc.

Track 205 comprises a pullback from a catheter position where a catheter 9 extends from the inferior vena cava (IVC) 204 to the superior vena cava (SVC) 203 via the right atrium (RA) 202. Thus, track 205 is through the sequence SVC-RA-IVC. Optionally, track 205 represents an initial pullback track, for example, one used with a catheter which reaches the heart via the inferior vena cava. This track provides the potential advantage of a wide base of sampling points with relatively little need for maneuvering, potentially increasing a likelihood of finding an unambiguous match between the two images.

Track 210 begins from a position with the catheter tip curved slightly and advanced so that it lodges in the right atrial appendage (RAA). Accordingly, track 210 extends through the sequence RAA-RA-IVC.

Track 215 begins from a position with the catheter passing from the right atrium to enter the right ventricle (RV) 202A, bending through it, and finally reaching to enter the main pulmonary artery (MPA). The bend in the right ventricle in particular provides a potentially useful landmark.

Figure 14:
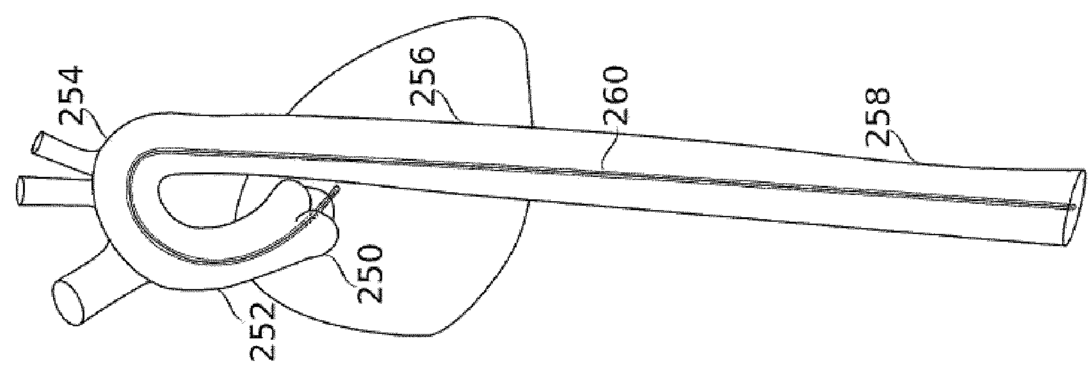
FIG. 14 is a diagrammatic view of a catheter track within a heart, according to aspects of the present disclosure.

Reference is now made to FIG. 14, which schematically represents the course of a pre-determined catheter track through regions of the aorta, according to some embodiments of the present disclosure.

Catheter track 260 is an example of how a catheter probe 11 may be moved through portions of an aorta in order to quickly register between the two images. Roughly, track 260 also corresponds to a catheter configuration (not shown separately) before pullback. The correspondence is not perfect, due, for example, to oscillations of the free catheter end, effects of catheter mechanical properties, etc.

Track 260 comprises a pullback from a catheter position where a catheter 9 extends from the aortic valve 250 back through the ascending aorta 252, the transverse aortic arch 254, thoracic aorta 256, and abdominal aorta 258. This track provides the potential advantage of a well-defined landmark in the form of the crook corresponding to the transverse aortic arch 254. Optionally track 260 is defined at least partially as a characteristic track, wherein the characteristic crook of the aortic arch is used as a landmark.

Figure 16:
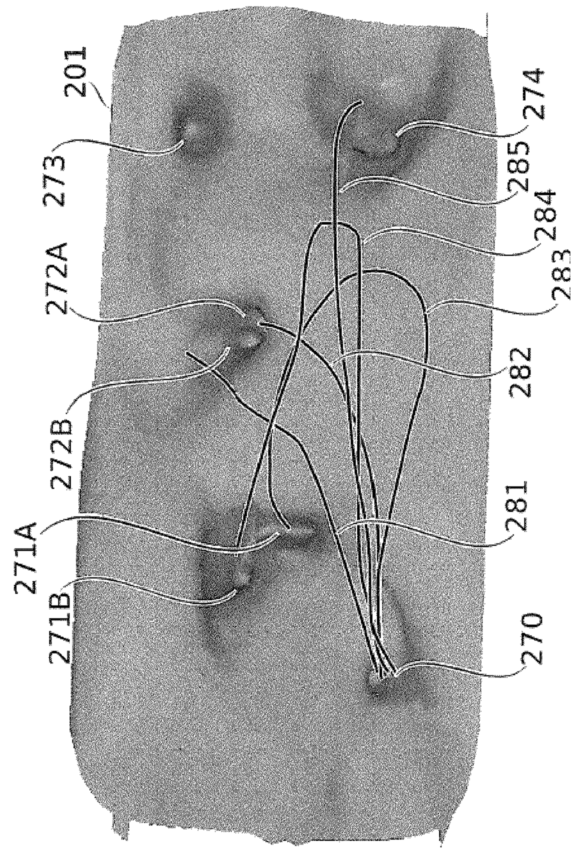
FIG. 16 is an interior perspective view of catheter tracks within an electro-anatomical image of a left atrium, according to aspects of the present disclosure.
Figure 15:
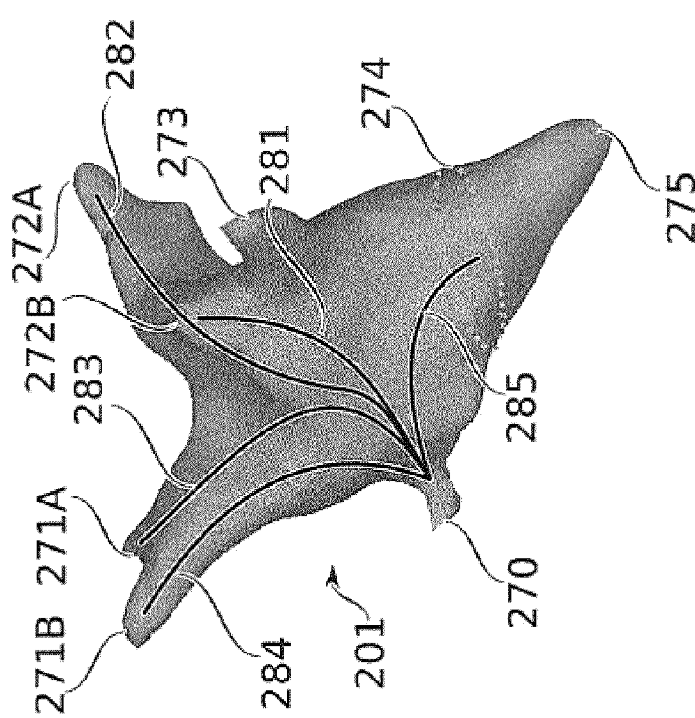
FIG. 15 is a perspective view of catheter tracks within an electro-anatomical image of a left atrium, according to aspects of the present disclosure.

Reference is now made to FIGS. 15 and 16, which schematically represent pre-determined catheter tracks to regions of the left atrium 201, according to some embodiments of the present disclosure. FIG. 15 represents in three dimensions the semi-transparent interior luminal surface of a left atrium 201. FIG. 16 represents the same interior luminal surface unwrapped and viewed from its interior side, for example as described in U.S. Provisional Patent Application 62/445,368, filed Jan. 12, 2017, and international patent application PCT/IB2018/050201, filed on Jan. 12, 2018, the contents of both of which are incorporated herein in their entirety.

In some embodiments, a catheter optionally enters a left atrium from a trans-septal crossing point 270 (e.g., the fossa ovalis). This provides one end of each of several tracks which connect trans-septal crossing point 270 to different landmarks of the left atrium. In particular:

Track 281 leads to the right superior pulmonary vein 272B.

Track 282 leads to the right inferior pulmonary vein 272A.

Track 283 leads to the left superior pulmonary vein 271A.

Track 284 leads to the left inferior pulmonary vein 271B. Tracks 283 and 284 appears to double back on themselves in FIG. 16 due to an artifact of the unwrapping.

Track 285 leads to the mitral valve 274.

Also indicated in the figures are positions of the mitral valve aperture 275, and the left atrial appendage 273. These features may also be used additionally and/or alternatively as landmarks for pre-determined tracks.

In some embodiments, only image points corresponding to one of these tracks are selected for use in the registration. In some embodiments, image points of two or more of these tracks are selected for use in the registration. As mentioned above, in some embodiments, the registration is not between image points but between point-cloud points. In some embodiments, the registration found for the selected points is used to register also other, non-selected, points.

In some embodiments, the registration transformation is based not only on the selected points, but the selected points are given larger weight than non-selected points. In some embodiments, the transform is used to transform only points of lesions, so that the lesions in the original heart are registered to (and shown on) an image of the remodeled heart. In some embodiments, locations of the lesions in the remodeled heart may be used by a physician as clues for finding gaps in the remodeled heart, e.g., by pacing first near gaps shown on the image. In some embodiments, the physician may close gaps between lesions in the remodeled heart based on the locations of the lesions shown on the image of the remodeled heart, e.g., by ablating in gaps shown on the image of the remodeled heart. A physician may determine the way to use the registered lesions based on his impression from the resemblance between the image of the remodeled heart and the results of the registration. To clarify this point, in some embodiments the physician may be supplied with three images: a first image taken in the ablation procedure, a second image taken in the re-do procedure, and a third image, which is the result of the registration of the first image to the second image. While the third image is the best fit between the two images under some fitting criteria (determined, e.g., by the weight given to the coherence condition, to a local scaling condition, to selected points, etc.) it is not identical to any of them, and particularly not to the second image. In some embodiments, the physician may be provided with a display of the third image overlaid on the second image, so he can visually judge the accuracy of the registration. In some embodiments, a value indicative of the fit quality between the second and third image may be attributed to the registration, and the physician may take this value into consideration in deciding what use he is making of the registration. In some embodiments, the value may be the numerical value of the cost function minimized to obtain the third image, and/or a verbal indication of the fit quality based on the size of this numerical value.

Figure 17:
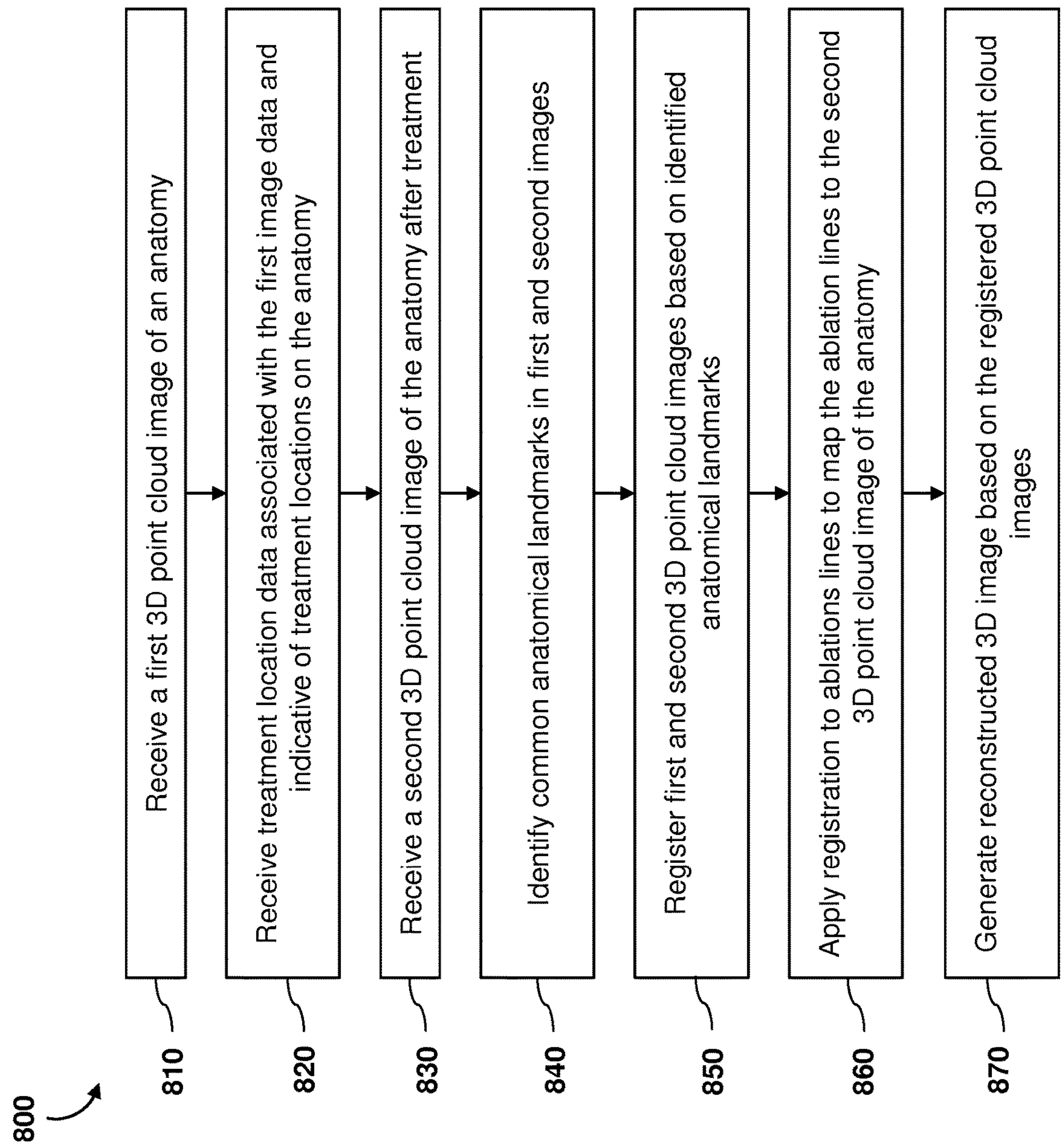
FIG. 17 is a flow diagram illustrating a method for co-registering three-dimensional point clouds, according to aspects of the present disclosure.

FIG. 17 is a flow diagram illustrating a method 800 for co-registering first and second three-dimensional point cloud images of an anatomy. A three-dimensional point cloud image may comprise a collection of data points defined within a particular coordinate system (e.g., cartesian, geodesic, polar, etc.) Point cloud images may be characterized in part by a number and distribution of points, point density, and other characteristics. In step 810, the system receives a first 3D point cloud image of an anatomy, where the point cloud image is obtained using a plurality of electrodes on a catheter, as described above. In step 820, the system receives treatment location data associated with the first point cloud image. For example, the treatment location data may indicate which points in the point cloud are associated with a treatment location (e.g., an ablation point), or the treatment location data may define new or additional data points that indicate the treatment location. In step 830, the system receives a second 3D point cloud image of the anatomy, for example, after the anatomy has remodeled as a result of treatment. It will be understood that, in some embodiments, the first image comprises a point cloud image, or is based on a point cloud, while the second image is not a point cloud image, and vice versa. In step 840, the system identifies common anatomical landmarks in first and second images. As explained above, the identification can include receiving an input from a user interface or input device that indicates a position of the landmark in the respective image. In some embodiments, the input may be submitted by a user with a keyboard, mouse, track ball, touch screen display, joystick, or any other suitable input device.

In step 850, the system registers the first and second 3D point cloud images based on identified anatomical landmarks. In some embodiments, the registration is between points of that point-cloud and points of the other image. When both images are reconstructed from point clouds, the registration may be between points of one point-cloud to points of another point-cloud. In some embodiments, points of the image which are not included in the point cloud are not registered.

In some embodiments, distances between points may be Euclidian distances. Alternatively, distances between the points may be geodesic distances. In some embodiments, the points of each image may form a point cloud, and points of one image are transformed to points of other image using natural inter-point distances. In some embodiments, a natural distance between two points in an image may be defined as the length of the shortest path that goes between the two points only through the point cloud. A path going only through a cloud is referred to herein as an intra-cloud path. In some embodiments, the cloud may be segmented, in the sense that it includes distinct segments; for example, a central segment (e.g., left atrium) connected to each of a plurality of peripheral segments (e.g., pulmonary veins). The peripheral segments may be interconnected only by pathways passing into the central segment from one segment, and back out of it to the other. In such embodiments, two peripheral segments may have points that are nearby in the Euclidean sense, but the natural distance between them is long, as every intra-cloud path between them goes via the central segment. In such embodiments, measuring coherence (or other constraints on the relationships between distances between points in one image and distances between corresponding points in the other image) using natural distances may preserve the segmentation of the point cloud, so that the segmentation of the two images is used as a clue in the registration.

An example of a segmentation preserving method of registering one segmented point cloud to another similarly segmented point cloud may include steps of: assigning each point in each cloud to a segment in the cloud; and transforming each point to a position in a segmented cloud requiring that points assigned to a same segment in the first cloud are transformed to the corresponding segment in the other cloud and points assigned to different segments in the first cloud are transformed to different segments in the other cloud.

In some embodiments, a segmentation preserving transform may be achieved by minimizing high spatial frequency components of the transform. For example, the transform may be decomposable to spatial frequency components, and a cost function may assign high cost to high frequency components, so that the obtained transform has relatively small or no components of high spatial frequency.

In step 860, as a result of registering the first and second point cloud images, the treatment locations (e.g., ablation lines) can be registered to the second point cloud image in order to show the updated locations resulting from movement in the remodeled anatomy. In step 870, a 3D image is generated based on the second image with an indication of the mapped treatment locations overlaid on the 3D image.

Figure 18:
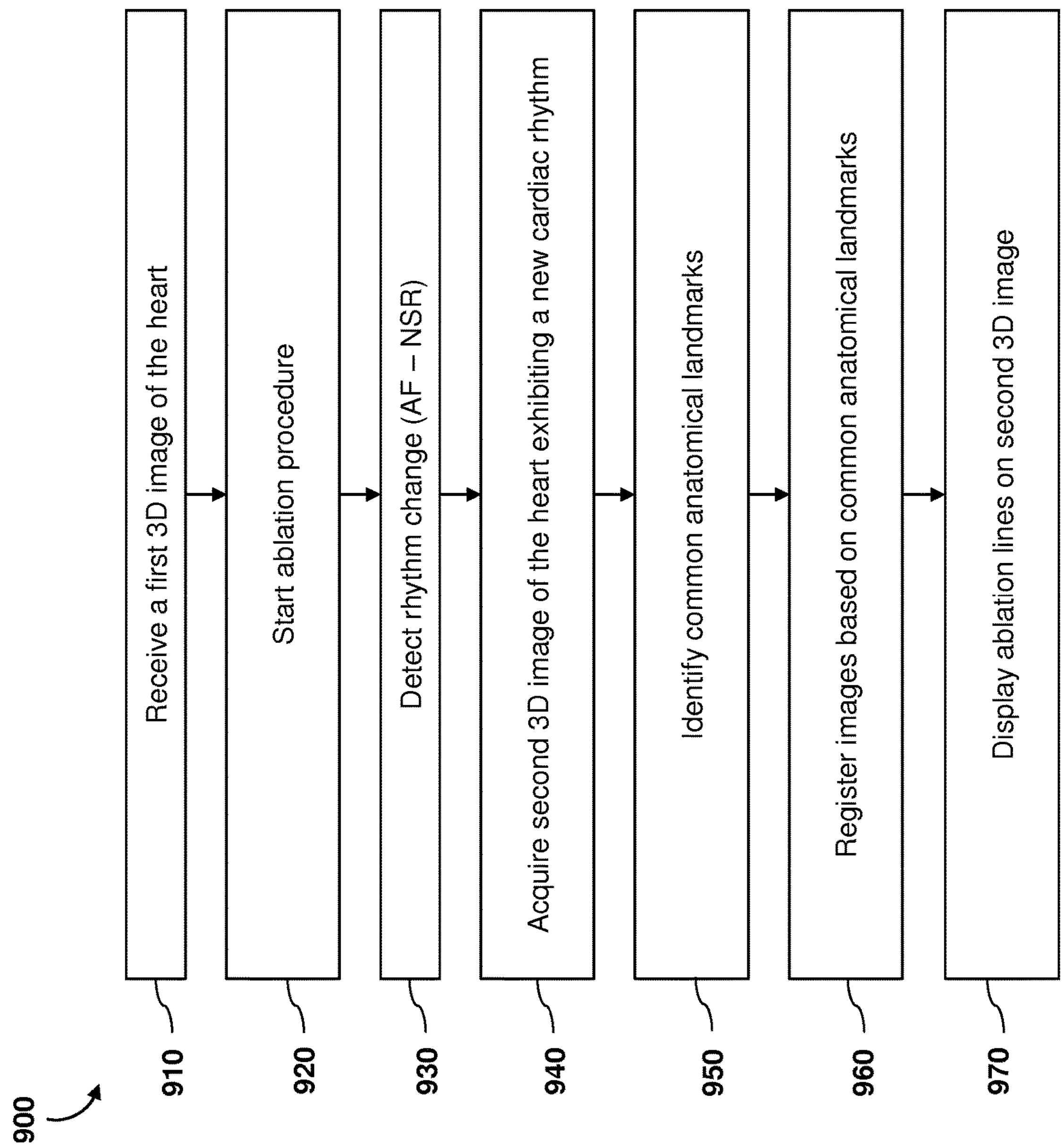
FIG. 18 is a flow diagram illustrating a method for co-registering electro-anatomical images of a heart in response to detecting a change in the heart rhythm, according to aspects of the present disclosure.

As mentioned above, heart remodeling can take place quickly, even before an ablation procedure is complete. Accordingly, in some instances, it may be beneficial to detect when the heart's rhythm has changed during the treatment procedure, and determine whether remodeling has taken place as a result. By monitoring the rhythm and geometry of the heart, mid-treatment remodeling of the heart can be compensated for, and the treatment plan can be adjusted accordingly to increase the quality of the treatment procedure. FIG. 18 is a flow diagram illustrating a method 900 for co-registering first and second three-dimensional electro-anatomical images of an anatomy during a treatment procedure based on a detection of a heart rhythm change.

In step 910, the system receives a first 3D image of the heart, for example, before an ablation procedure. In step 920, the ablation procedure begins. In step 930, the system detects a rhythm change in the heart. For example, the rhythm of the heart may change from an arrhythmic, or AF rhythm to a normal sinus rhythm (NSR). In some embodiments, the system may detect the change in rhythm by obtaining electrophysiological (EP) data using the electrodes on the catheter. In other embodiments, other detection methods are coupled to the system, such as external body patch electrodes, or an ECG monitor. In step 940, in response to detecting a change in heart rhythm, a second 3D image of the heart is obtained. In step 950, common anatomical landmarks are identified in the first and second 3D images to be used in determining a transformation between the two images. In step 950, the system registers the first and second 3D images using a determined transformation that is based on the common identified landmarks. It will be understood that, in some embodiments, the registration achieved in step 960 is performed based on common catheter tracks, or on other parameters contemplated by the present disclosure.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

The invention claimed is:

1. A system for co-registering electro-anatomical images, comprising:

- a user display; and
- a processor circuit in communication with the user display and configured to:
  - receive a first electro-anatomical image of an anatomy, the first electro-anatomical image generated based on electro-anatomical data obtained using two or more electrodes positioned on a catheter;
  - receive treatment location data indicating treatment locations with respect to the first electro-anatomical image, the treatment location data based on the electro-anatomical data obtained using the two or more electrodes positioned on the catheter;
  - receive a second electro-anatomical image of the anatomy after the anatomy has remodeled;
  - determine a non-rigid transformation that transforms the first electro-anatomical image to the second electro-anatomical image of the remodeled anatomy;
  - apply the non-rigid transformation to the treatment location data to map the treatment locations to the second electro-anatomical image of the remodeled anatomy; and
  - display the treatment locations mapped to the second electro-anatomical image on the user display.

2. The system of claim 1, wherein the processor circuit is configured to determine the non-rigid transformation based on a known distance between the two or more electrodes on the catheter.

3. The system of claim 1, wherein the processor circuit is configured to determine the non-rigid transformation based on a probabilistic correspondence model that assigns a probability of correspondence between a first point in the first electro-anatomical image and a second point in the second electro-anatomical image, and wherein the probabilistic correspondence model comprises a coherence condition in which a greater probability of correspondence is assigned to points near a same anatomical landmark identified in each of the first and second electro-anatomical images.

4. The system of claim 1, wherein the processor circuit is configured to:

- identify a landmark in the first electro-anatomical image;
- identify the landmark in the second electro-anatomical image; and
- determine the non-rigid transformation based on the landmark identified in the first and second electro-anatomical images.

5. The system of claim 4, further comprising a user input device in communication with the processor circuit, wherein the processor circuit is configured to:

- receive, from the user input device, a first input indicating a location of the landmark in the first electro-anatomical image;
- receive, from the user input device, a second input indicating a location of the landmark in the second electro-anatomical image; and
- determine the non-rigid transformation based on the received first and second inputs.

6. The system of claim 1, wherein the processor circuit is configured to:

associate, with respect to the first electro-anatomical image, a first plurality of electro-anatomical data points with a first catheter track;

associate, with respect to the second electro-anatomical image, a second plurality of electro-anatomical data points with a second catheter track, wherein the first catheter track is aligned with the second catheter track; and determine the non-rigid transformation based on a correspondence between the first and second catheter tracks.

7. The system of claim 6, further comprising a user input device in communication with the processor circuit, wherein the processor circuit is configured to:

receive, from the user input device, a first plurality of inputs indicating locations of the catheter while traveling along the first catheter track;

receive, from the user input device, a second plurality of inputs indicating locations of the catheter while traveling along the second catheter track; and determine the non-rigid transformation based on the first and second pluralities of inputs.

8. The system of claim 1, wherein the first electro-anatomical image comprises a first three-dimensional point cloud image of the anatomy, wherein the second electro-anatomical image comprises a second three-dimensional point cloud image of the anatomy, and wherein the processor circuit is configured to:

determine the transformation by registering points of the first point cloud image to corresponding points of the second point cloud image; and generate a reconstructed three-dimensional image based on the registered points of the first and second cloud images.

9. The system of claim 8, wherein the processor circuit is configured to determine the transformation based on natural inter-point distances.

10. The system of claim 9, wherein the processor circuit is configured to segment each of the first and second electro-anatomical images into a plurality of segments.

11. The system of claim 10, wherein the processor circuit is configured to:

assign the points of the first point cloud image to a segment;

assign the corresponding points of the second point cloud image to the same segment; and determine the transformation such that the points in the first point cloud image are transformed to the same segment in the second point cloud image.

12. The system of claim 1, wherein the processor circuit is configured to:

detect a physiological rhythm change in the anatomy, wherein the second electro-anatomical image represents the anatomy exhibiting the changed physiological rhythm.

13. A method for co-registering electro-anatomical images, comprising:

receiving, at a processor circuit in communication with a user display, a first electro-anatomical image of an anatomy, the first electro-anatomical image generated based on electro-anatomical data obtained using two or more electrodes positioned on a catheter;

receiving, at the processor circuit, treatment location data indicating treatment locations with respect to the first electro-anatomical image, the treatment location data based on the electro-anatomical data obtained using the two or more electrodes positioned on the catheter;

receiving, at the processor circuit, a second electro-anatomical image of the anatomy after the anatomy has remodeled;

determining a non-rigid transformation that transforms the first electro-anatomical image to the second electro-anatomical image of the remodeled anatomy;

applying the non-rigid transformation to the treatment location data to map the treatment locations to the second electro-anatomical image of the remodeled anatomy; and displaying the treatment locations mapped to the second electro-anatomical image on the user display.

14. The method of claim 13, wherein determining the non-rigid transformation comprises determining the non-rigid transformation based on a known distance between the two or more electrodes on the catheter.

15. The method of claim 13, wherein determining the non-rigid transformation comprises determining the non-rigid transformation based on a probabilistic correspondence model that assigns a probability of correspondence between a first point in the first electro-anatomical image and a second point in the second electro-anatomical image, and wherein the probabilistic correspondence model comprises a coherence condition in which a greater probability of correspondence is assigned to points near a same anatomical landmark identified in each of the first and second electro-anatomical images.

16. The method of claim 13, further comprising:

identifying a landmark in the first electro-anatomical image;

identifying the landmark in the second electro-anatomical image; and determining the non-rigid transformation based on the landmark identified in the first and second electro-anatomical images.

17. The method of claim 13, further comprising:

associating, with respect to the first electro-anatomical image, a first plurality of electro-anatomical data points with a first catheter track;

associating, with respect to the second electro-anatomical image, a second plurality of electro-anatomical data points with a second catheter track, wherein the first catheter track is aligned with the second catheter track; and determining the non-rigid transformation based on a correspondence between the first and second catheter tracks.

18. The method of claim 13, wherein receiving the first electro-anatomical image comprises receiving a first three-dimensional point cloud image of the anatomy, wherein receiving the second electro-anatomical image comprises receiving a second three-dimensional point cloud image of the anatomy, and wherein the method further comprises:

determining the transformation by registering points of the first point cloud image to corresponding points of the second point cloud image; and generating a reconstructed three-dimensional image based on the registered points of the first and second cloud images.

19. The method of claim 13, further comprising:

detecting a physiological rhythm change in the anatomy, wherein the second electro-anatomical image represents the anatomy exhibiting the changed physiological rhythm.

* * * * *